United States Patent [19]

Pittet et al.

[11] Patent Number: 4,634,595

[45] Date of Patent: * Jan. 6, 1987

[54] THIOALKANOIC ACID ESTERS OF PHENYLALKANOLS

[75] Inventors: Alan O. Pittet, Atlantic Highlands; Ranya Muralidhara, Fair Haven; Manfred H. Vock, Locust; Domenick Luccarelli, Jr., Neptune; Kevin P. Miller; Charles Wiener, both of Middletown, all of N.J.

[73] Assignee: International Flavors & Fragrances Inc., New York, N.Y.

[*] Notice: The portion of the term of this patent subsequent to May 20, 2003 has been disclaimed.

[21] Appl. No.: 778,506

[22] Filed: Sep. 20, 1985

[51] Int. Cl.⁴ .................... A23L 1/226; A23L 1/231; A23L 1/235
[52] U.S. Cl. .................................... 426/535; 560/152
[58] Field of Search ........................ 426/535; 560/152

[56] References Cited

U.S. PATENT DOCUMENTS 4,557,941 12/1985 Pittet et al. .................. 426/535
4,590,082 5/1986 Pittet et al. .................. 426/535

Primary Examiner—Joseph Golian
Attorney, Agent, or Firm—Arthur L. Liberman

[57] ABSTRACT

Described is a process for augmenting or enhancing the aroma or taste of a foodstuff comprising the step of adding to a foodstuff, a thioalkanoic acid ester of a phenylalkanol defined according to the structure:

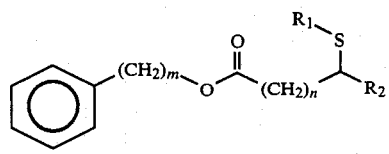

wherein M represents an integer selected from the group consisting of 1, 2 or 3; N is 0, 1 or 2; $R_1$ represents methyl or hydrogen and $R_2$ represents methyl or hydrogen.

11 Claims, 19 Drawing Figures

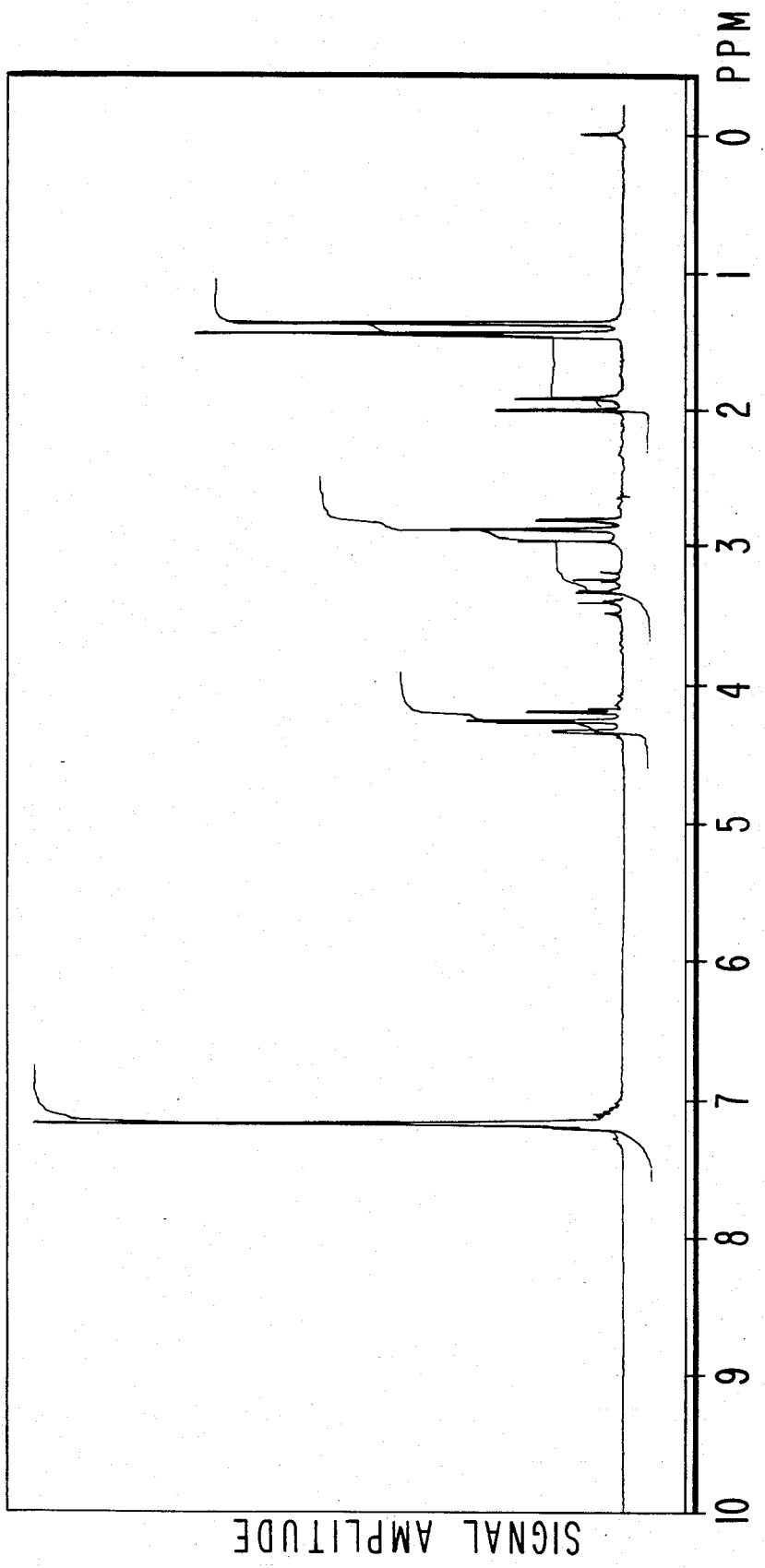

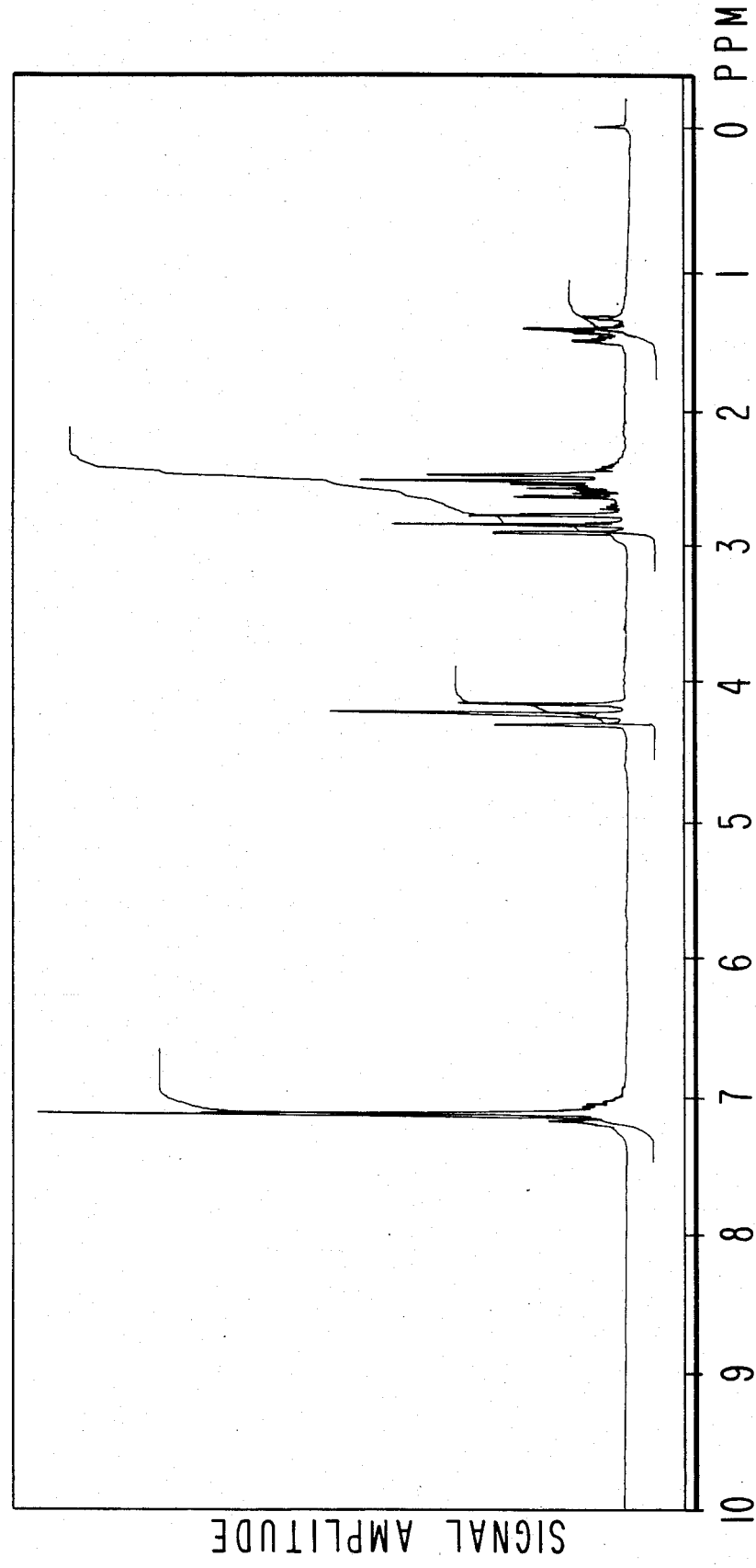

GLC PROFILE FOR EXAMPLE IV CRUDE

GLC PROFILE FOR EXAMPLE III CRUDE

NMR SPECTRUM FOR EXAMPLE III

FIG. 7 NMR SPECTRUM FOR EXAMPLE V.

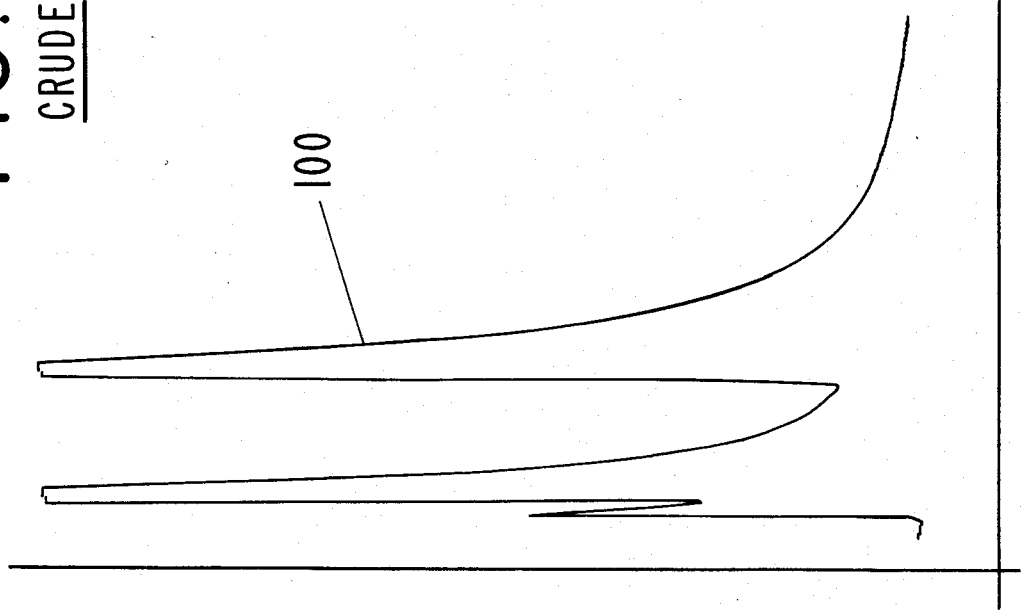
FIG.10 CRUDE
100
GLC PROFILE FOR EXAMPLE VII.
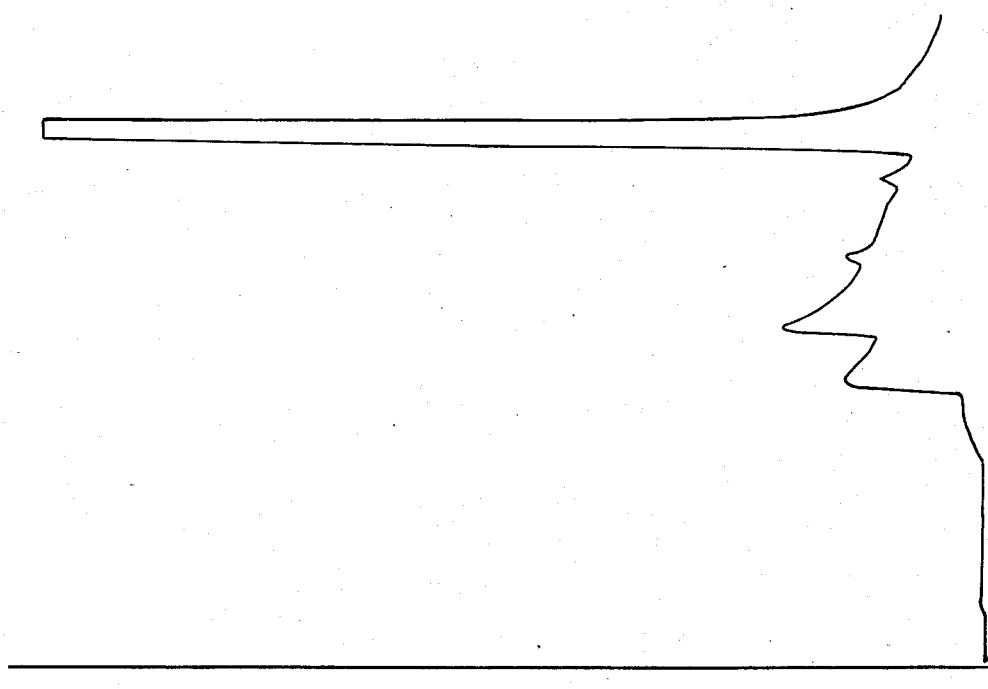
FIG.8
GLC PROFILE FOR EXAMPLE VI. CRUDE

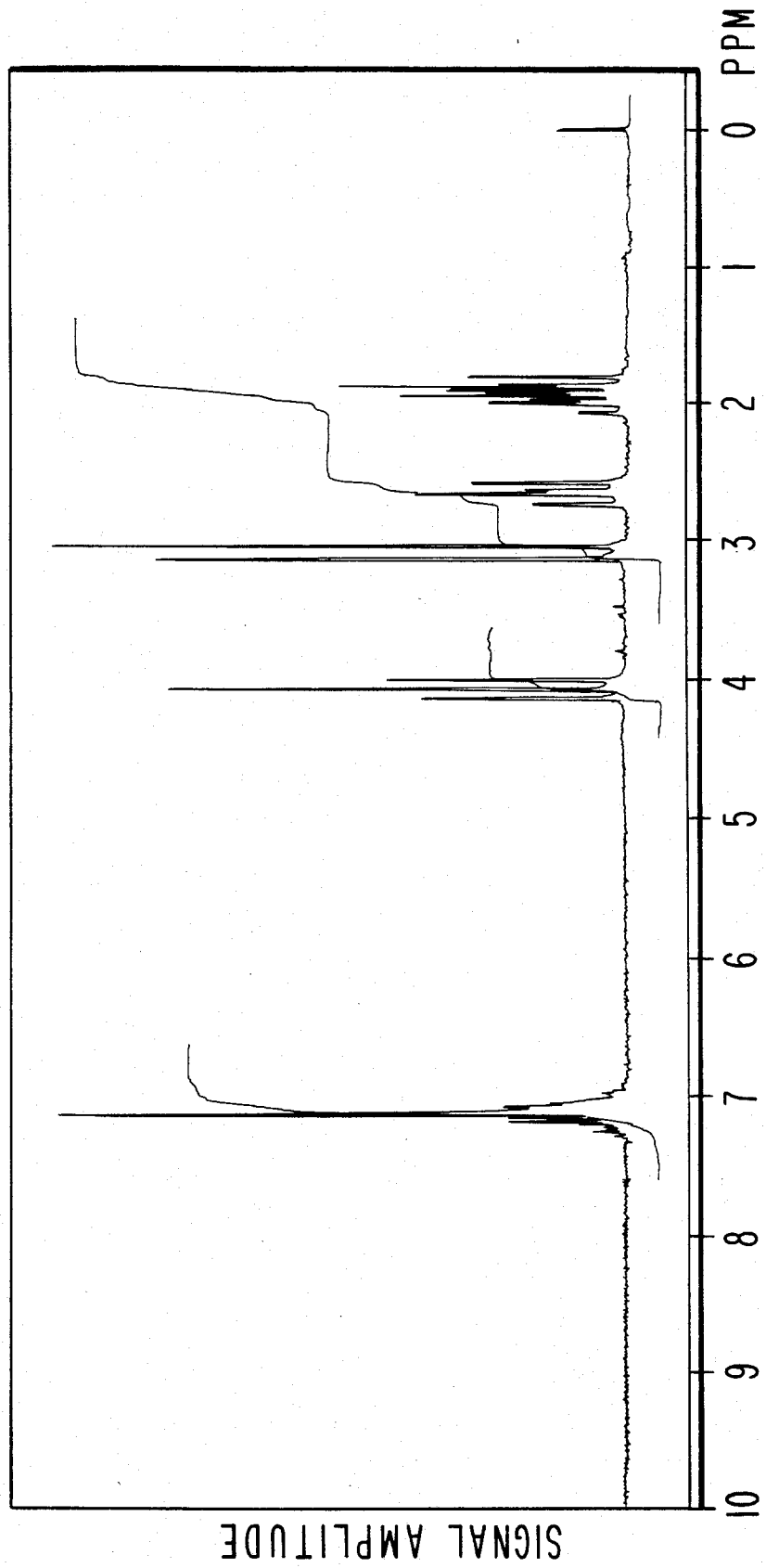

GLC PROFILE FOR FRACTION 3 OF EXAMPLE IX.

GLC PROFILE FOR EXAMPLE VIII CRUDE

NMR SPECTRUM FOR EXAMPLE VIII.

GLC PROFILE FOR FRACTION 4 OF EXAMPLE IX.

GLC PROFILE FOR FRACTION 4 OF EXAMPLE IX.

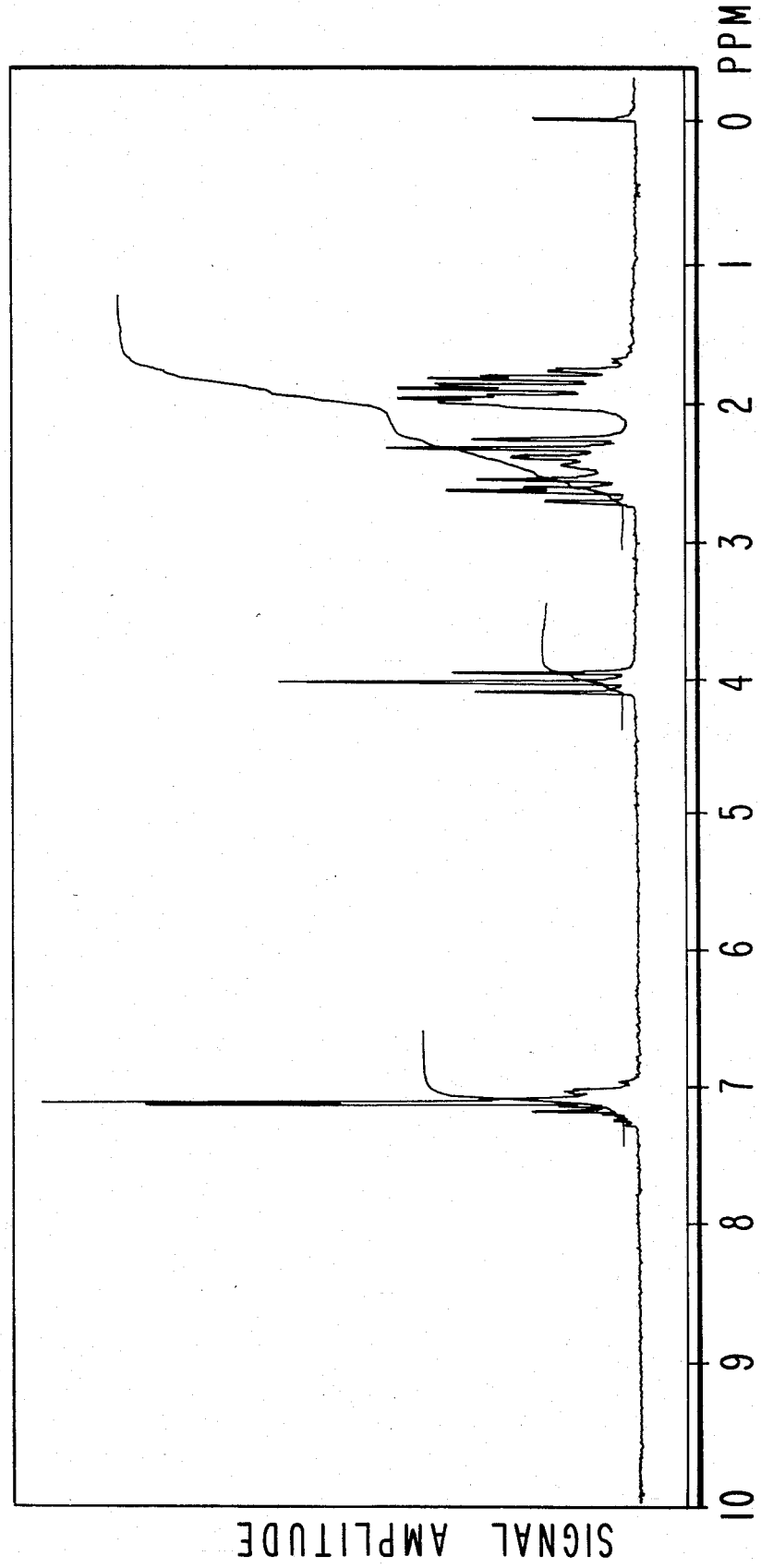
FIG. 16 NMR SPECTRUM FOR FRACTION 4 OF EXAMPLE IX

GLC PROFILE FOR FRACTION 5 OF EXAMPLE X.

NMR SPECTRUM FOR FRACTION 4 OF EXAMPLE X

THIOALKANOIC ACID ESTERS OF PHENYLALKANOLS

BACKGROUND OF THE INVENTION

Described are thioalkanoic acid esters of phenylalkanols defined according to the structure:

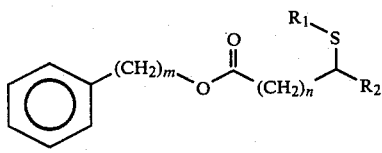

wherein M represents an integer selected from the group consisting of 1, 2 or 3; N is 0, 1 or 2; $R_1$ represents methyl or hydrogen and $R_2$ represents methyl or hydrogen and uses thereof in augmenting or enhancing the aroma or taste of foodstuffs.

Artificial flavoring agents for foodstuffs have received increasing attention in recent years. In many areas, such food flavoring agents are preferred over natural flavoring agents at least in part, because of the uniform flavor that may be so obtained. For example, natural food flavoring agents such as extracts, essences, concentrates and the like are often subject to wide variations due to changes in quality and type and treatment of the raw materials. Such variations can be reflected in the end product and results in unreliable flavor characteristics and uncertainty as to consumer acceptance and cost. Additionally, the presence of the natural product in the ultimate food may be undesirable because of the increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavoring development in many foods is not understood. This is notable in products having floral, rosy, roasted, peanut, roasted peanut, sesame seed, roasted almond, sulfury, roasted sesame, oniony, durian, charbroiled, coconut/macaroon, beer, yeasty and hydrolyzed vegetable protein-like aroma and taste nuances.

Reproduction of floral, rosy, roasted, peanut, roasted peanut, sesame seed, roasted almond, sulfury, roasted sesame, oniony, durian, charbroiled, burnt, coconut/macaroon, beer, yeasty and hydrolyzed vegetable protein-like aroma and taste nuances has been the subject of long and continuous searches by those engaged in the production of foodstuffs. The severe shortage of food, especially protein foods, in many parts of the world has given rise to the need for utilizing non-meat sources of proteins and making such proteins as palatable as possible. Hence, materials which will closely simulate or exactly reproduce the flavor and aroma of hydrolyzed vegetable protein and even roasted peanut, peanut butter, caramel, cocoa, chocolate, roasted almond, roasted nut, sesame seed, coffee, grape, cashew juice, hazel nut, durian, charbroiled, yeasty, beer and black bread-like flavored foodstuffs are required.

Moreover, there are a great many meat containing or meat based foods presently distributed in a preserved form. Examples of these are condensed soups, dry soup mixes, dry meat, freeze dried or lyophylized meats, packaged gravies and the like. While these products contain meat or meat extracts, the fragrance, taste and other organoleptic factors are often impaired by the processing operation and it is desirable to supplement or enhance the flavors of these preserved foods with versatile materials which have hydrolyzed vegetable protein-like and roasted aroma and taste nuances.

Food flavors in the thioalkanoic acid ester area are known in the prior art.

Thus, application for U.S. Letters Patent Ser. No. 715,344 filed on Mar. 25, 1985 now U.S. Pat. No. 4,557,941 issued on Dec. 10, 1985 discloses the genus of compounds defined according to the generic structure:

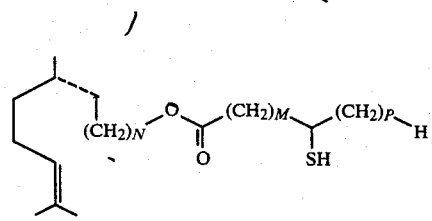

wherein N represents 0 or 1; M represents 0, 1 or 2; P represents 0 or 1; and the dashed line represents a carbon-carbon single bond or a carbon-carbon double bond with the proviso that when N is 0 then the dashed line represents a carbon-carbon single bond and uses thereof in augmenting or enhancing the aroma or taste of foodstuffs.

Further, U.S. Pat. No. 4,426,403 discloses the genus of compounds defined according to the structure:

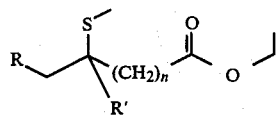

wherein R and R' represent hydrogen or $C_1$-$C_3$ alkyl as food flavorants, particularly in the fruity, vegetable or green pine needle aroma and taste area.

U.S. Pat. No. 3,870,800 relates to the processes for augmenting or enhancing the aroma or taste of foodstuffs using methylthio butanoic acid derivatives. U.S. Pat. No. 3,904,556, at Example XVII thereof states that ethyl-4-(methylthio)butyrate may be added to a cheese sauce to increase the notes usually present in the surface ripened cheese and to increase the cheese flavor intensity. In Example XX it is further stated that this compound, ethyl-4-(methylthio)butyrate is added to tobacco to enhance the pineapple character of a fruit flavor for tobacco.

U.S. Pat. No. 3,879,562 issued on Apr. 22, 1975 and the reissue patent thereof, U.S. Pat. No. Re. 30,370 issued on Aug. 12, 1980 disclose the genus of compounds having the structure:

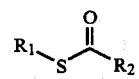

wherein $R_1$ represents alkyl, cycloalkyl, aryl, aralkyl, alkaryl, or alkenyl and $R_2$ represents alkyl, alkyl thioalkyl, aralkyl, alkaryl, or aryl in augmenting or enhancing the aroma or taste of various foodstuffs.

McFadden, et al, Analytical Chemistry 37,560, have suggested the presence of methyl thiohexanoate and thioheptanoate in oil derived from hops, and Buttery, et al, have reported similar work in J. Chromatography 18,399. Schultz, Day, and Libbey, "The Chemistry and Physiology of Flavors", Westport, Conn.: Avi. Publishing Company 1967, at page 412 disclose thioesters useful in flavoring.

Nevertheless, nothing in the prior art discloses the thioalkanoic acid esters of phenylalkanols of our invention or their unexpected, unobvious or advantageous uses in augmenting or enhancing the aroma or taste of foodstuffs.

BRIEF DESCRIPTION OF THE DRAWINGS

FIG. 1 is the NMR spectrum for the compound having the structure:

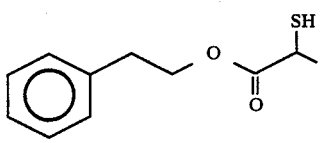

prepared according to EXAMPLE I. (Conditions: Field strength: 100 MHz; solvent: CFCl$_3$).

FIG. 2 is the NMR spectrum for the compound having the structure:

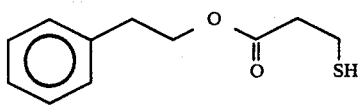

produced according to Example II. (Conditions: Field strength: 100 MHz; solvent: CFCl$_3$).

Figure 3:
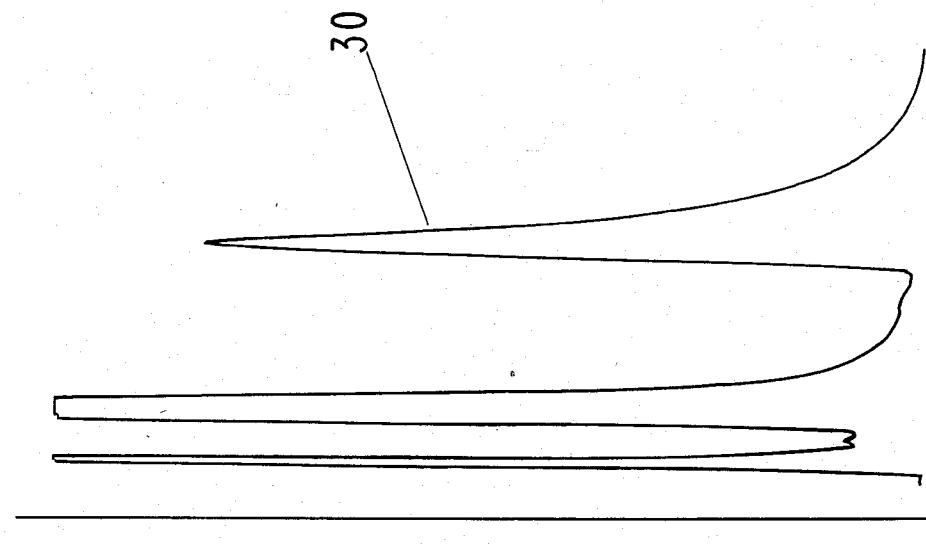

FIG. 3 is the GLC profile for the crude reaction product of Example III containing the compound having the structure:

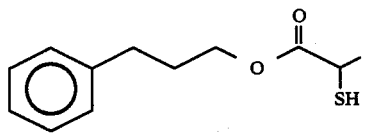

(Conditions: 8'×0.25" carbowax column programmed at 220° C. isothermal).

Figure 4:
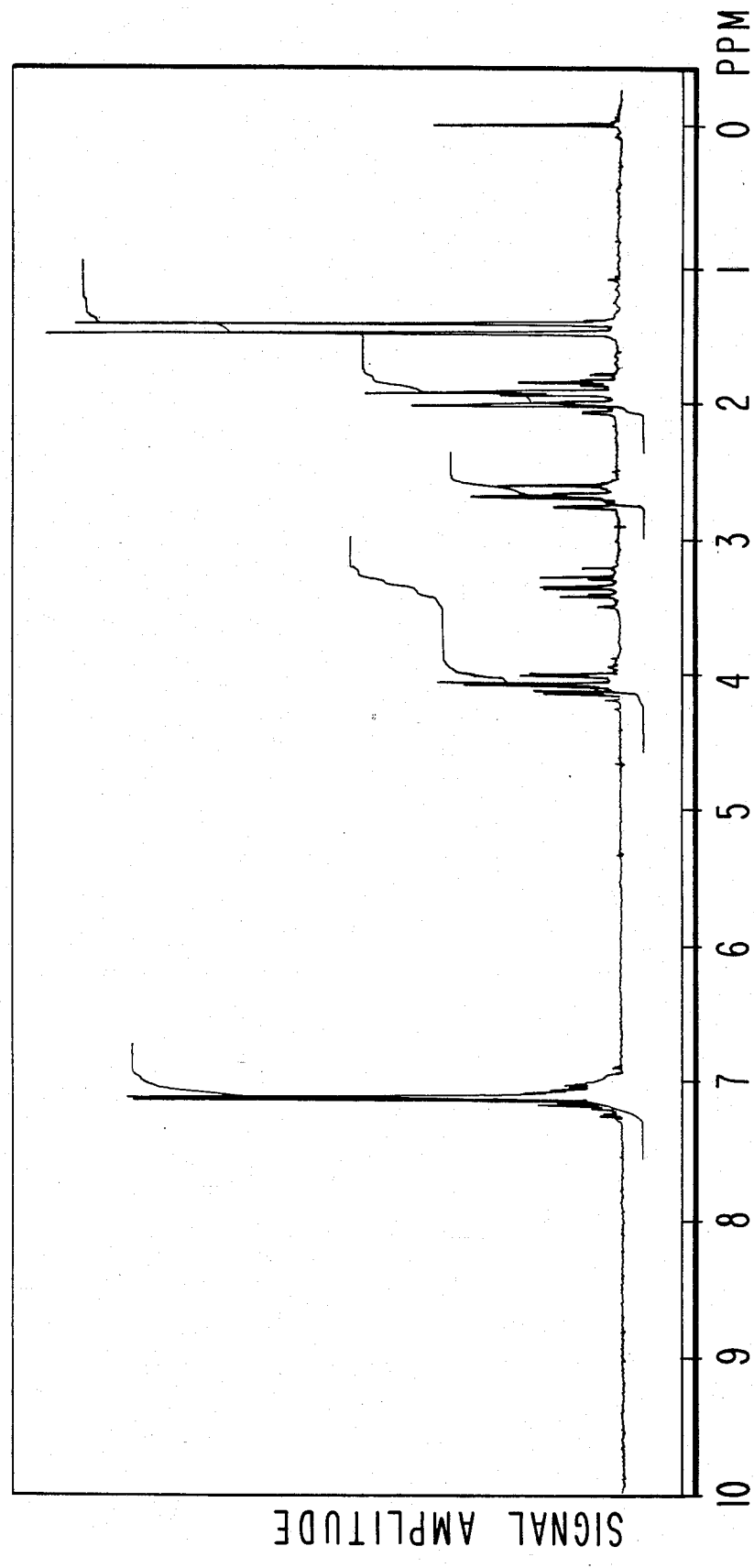

FIG. 4 is the NMR spectrum for the compound having the structure:

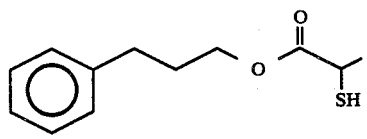

produced according to Example III. (Conditions: Field strength: 100 MHz; solvent: CFCl$_3$).

Figure 5:
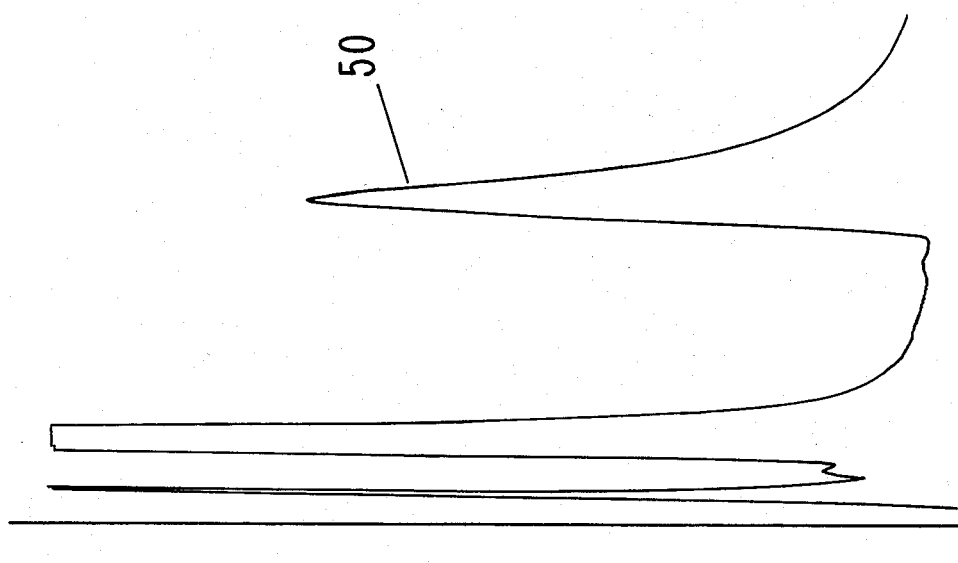

FIG. 5 is the GLC profile for the crude reaction product of Example IV containing the compound having the structure:

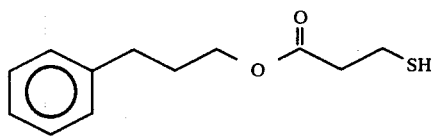

(Conditions: 8'×0.25" carbowax column programmed at 220° C. isothermal).

Figure 6:
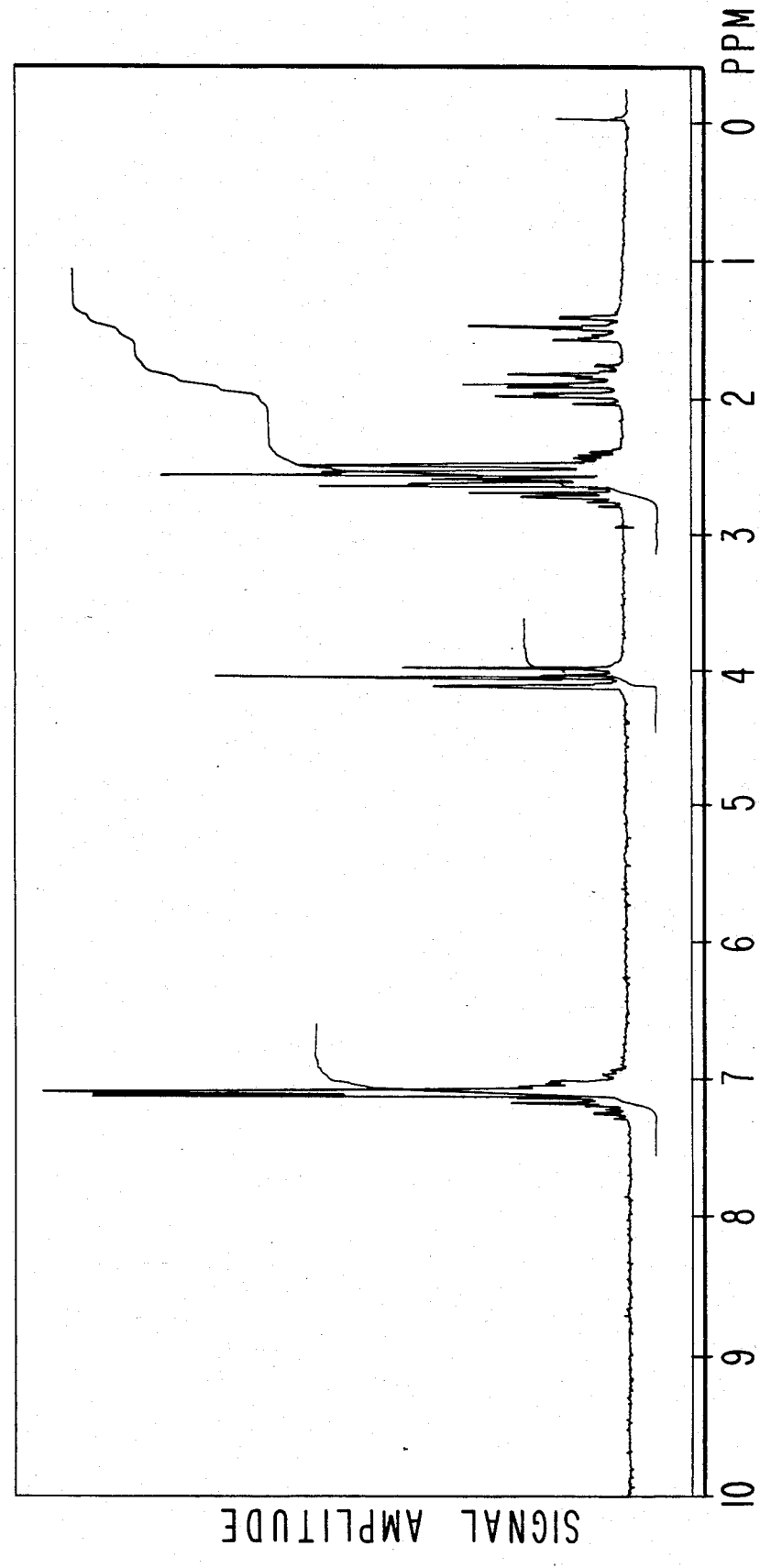

FIG. 6 is the NMR spectrum for the compound having the structure:

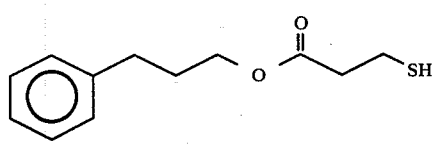

produced according to Example IV. (Conditions: Field strength: 100 MHz; solvent: CFCl$_3$).

Figure 7:
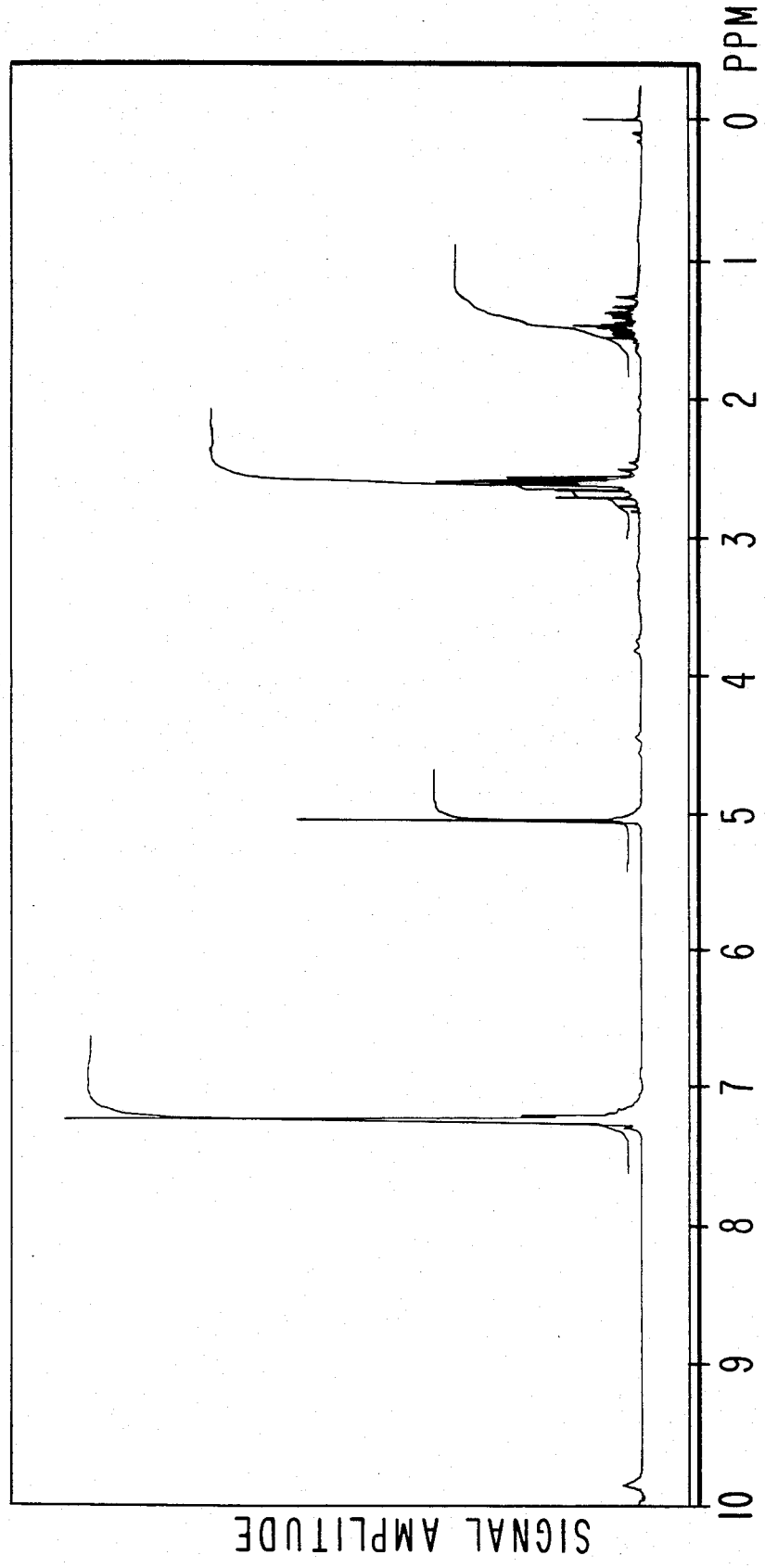

FIG. 7 is the NMR spectrum for the compound having the structure:

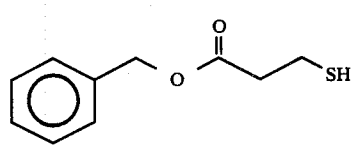

produced according to Example V. (Conditions: Field strength: 100 MHz; solvent: CFCl$_3$).

FIG. 8 is the GLC profile for the crude reaction product of Example VI having the structure:

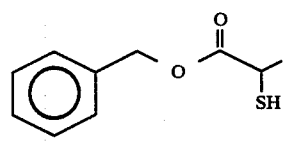

(Conditions: 8'×0.125" SE-30 column programmed at 100°-220° C. at 8° C. per minute).

Figure 9:
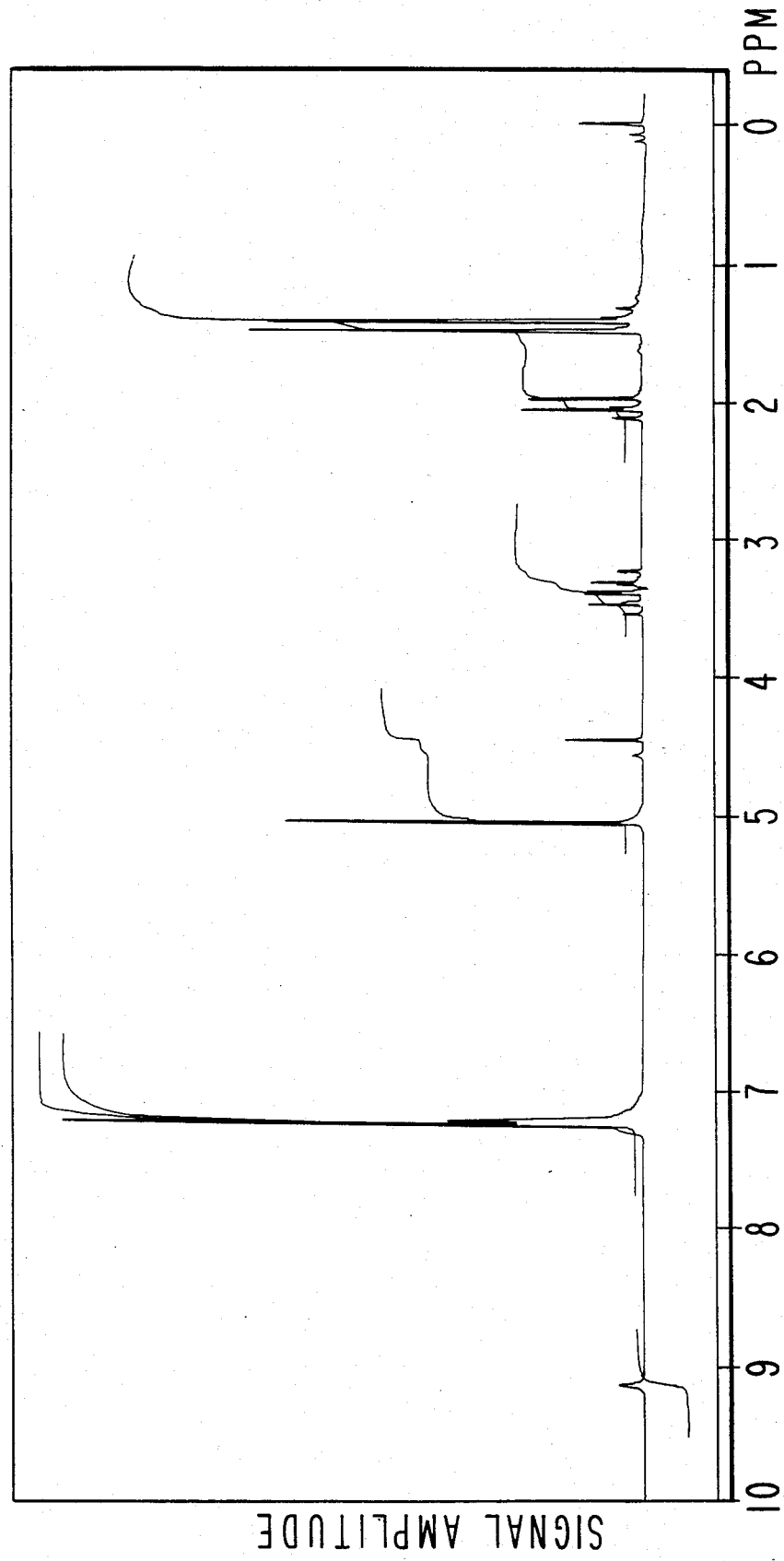

FIG. 9 is the NMR spectrum for the compound having the structure:

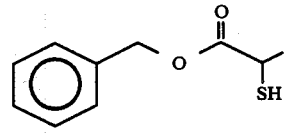

produced according to Example VI. (Conditions: Field strength: 100 MHz; solvent: CFCl$_3$).

FIG. 10 is the GLC profile for the crude reaction product of Example VII containing the compound having the structure:

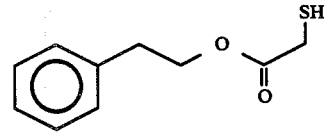

(Conditions: 8'×0.25" carbowax column programmed at 220° C. isothermal).

FIG. 11 is the NMR spectrum for the compound having the structure:

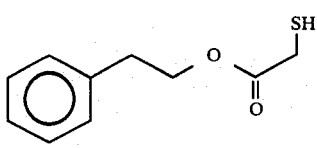

produced according to Example VII. (Conditions: Field strength: 100 MHz; solvent: CFCl₃).

Figure 12:
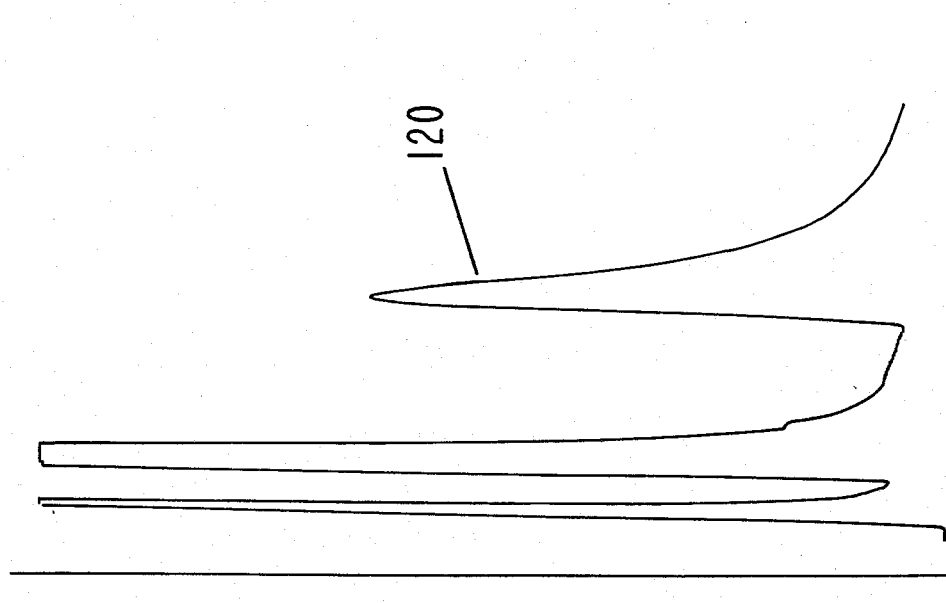

FIG. 12 is the GLC profile for the crude reaction product of Example VIII containing the compound having the structure:

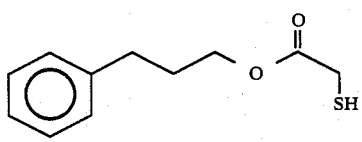

(Conditions: 8'×0.25" carbowax column programmed at 220° C. isothermal).

Figure 13:
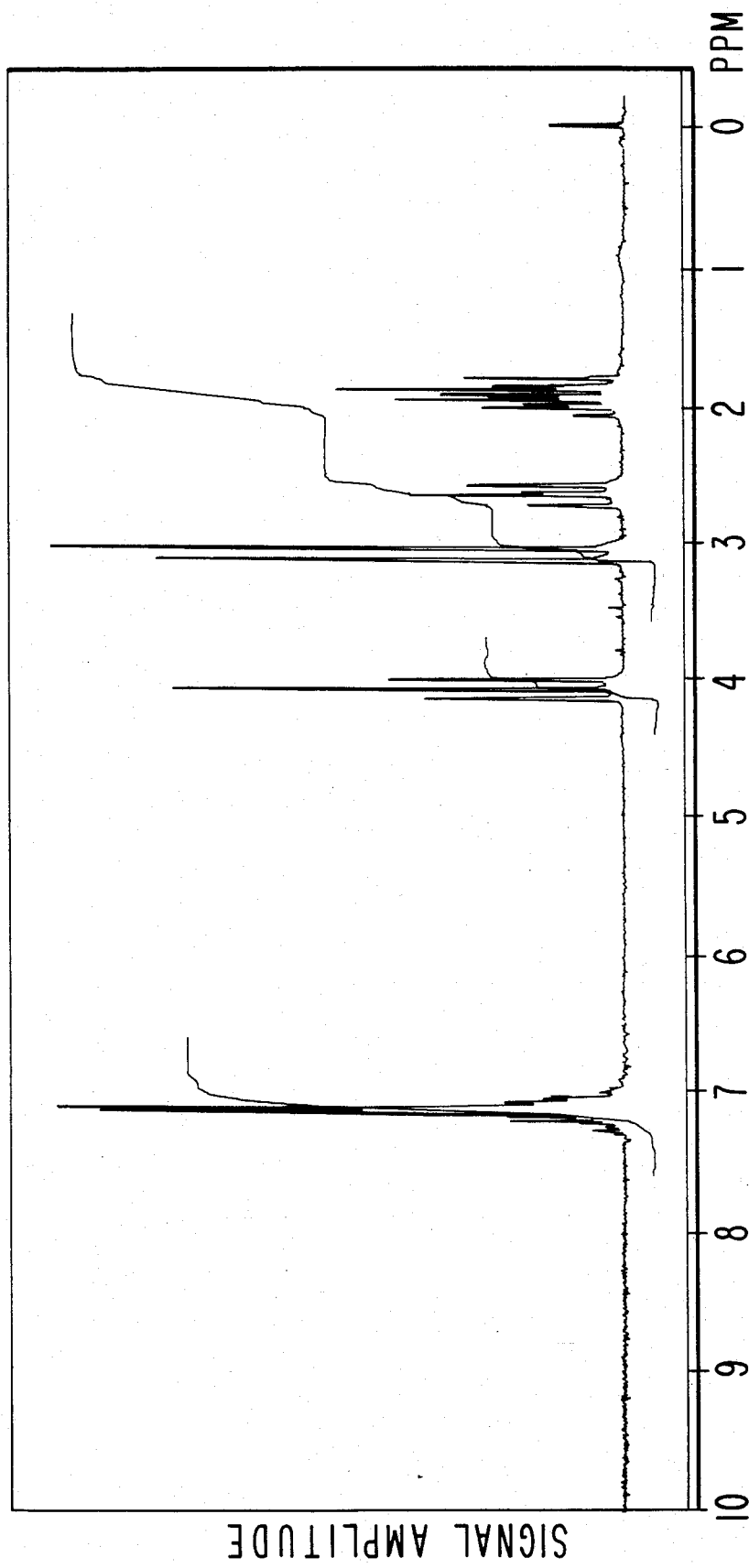

FIG. 13 is the NMR spectrum for the compound having the structure:

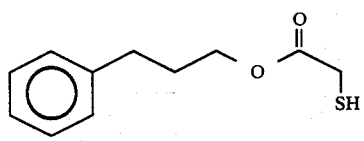

produced according to Example VIII. (Conditions: Field strength: 100 MHz; solvent: CFCl₃).

Figure 14:
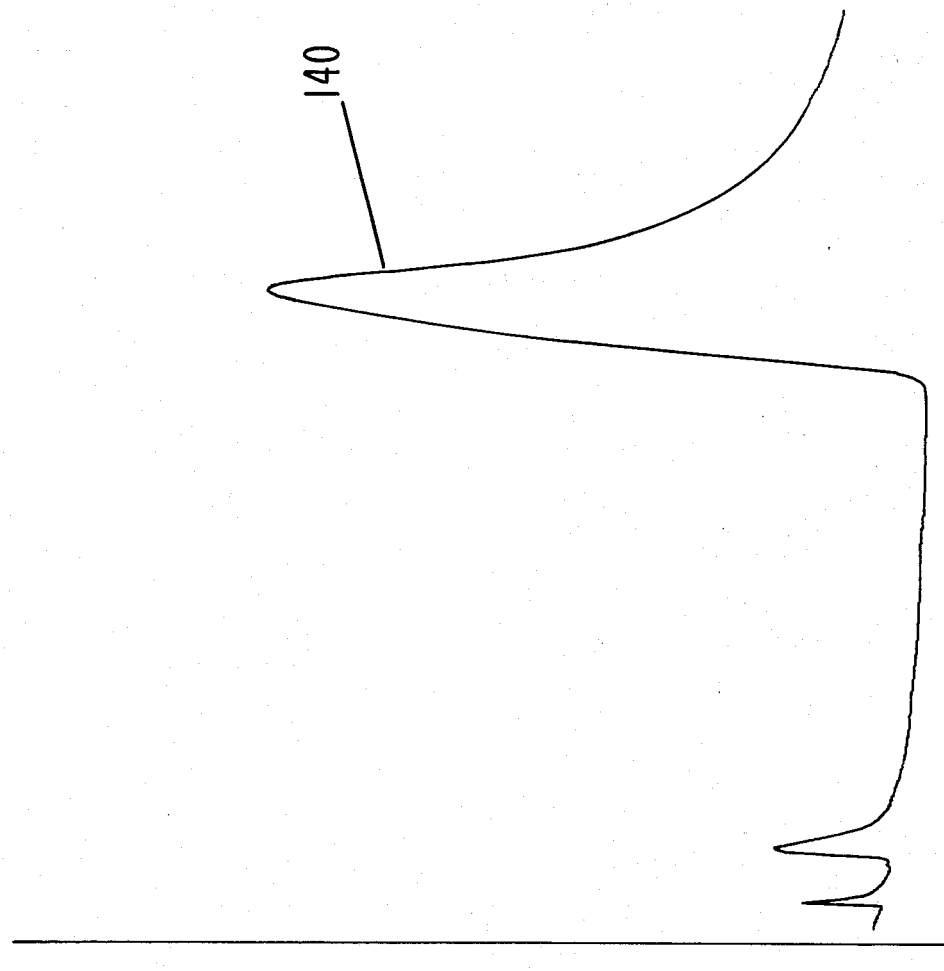

FIG. 14 is the GLC profile for fraction 3 of the distillation product of the reaction product of Example IX containing the compound having the structure:

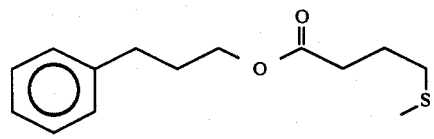

(Conditions: 8'×0.25" carbowax column programmed at 220° C. isothermal).

Figure 15:
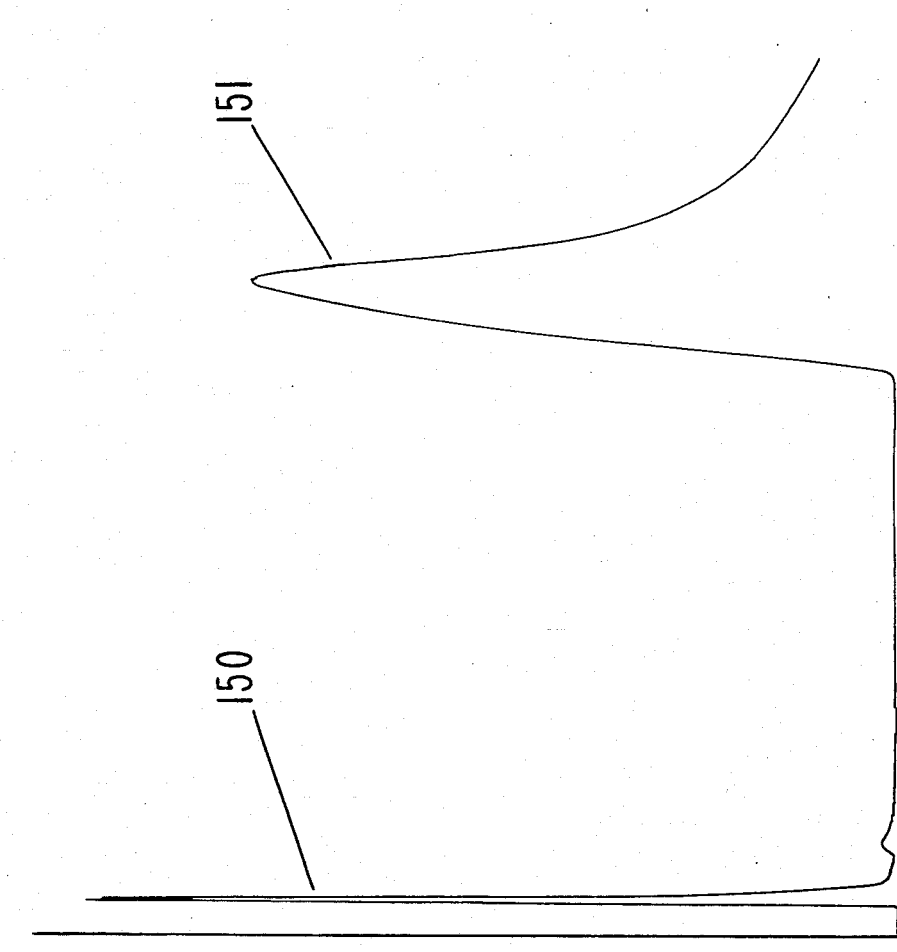

FIG. 15 is the GLC profile for fraction 4 of the distillation product of the reaction product of Example IX containing the compound having the structure:

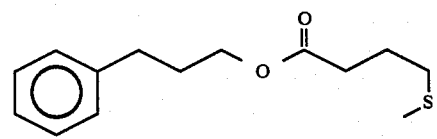

(Conditions: 8'×0.25" carbowax column programmed at 220° C. isothermal).

FIG. 16 is the NMR spectrum for the compound having the structure:

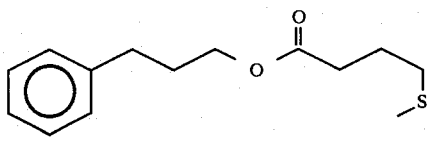

produced according to Example IX (fraction 4). (Conditions: Field strength: 100 MHz; solvent: CFCl₃).

Figure 17:
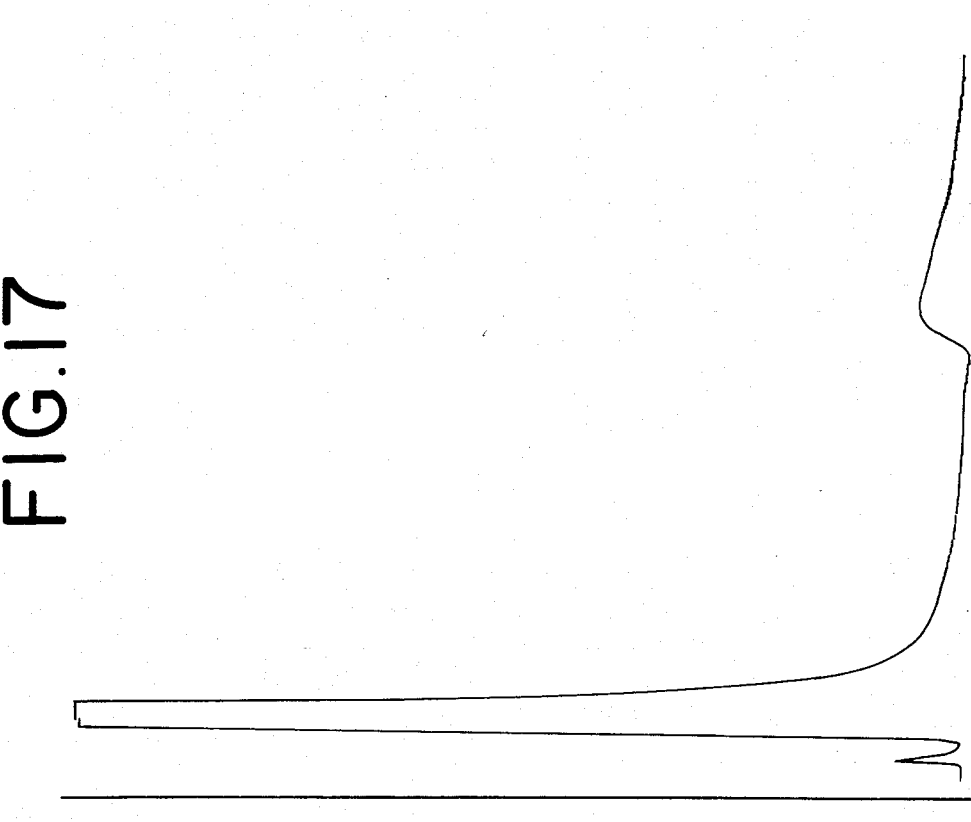

FIG. 17 is the GLC profile for fraction 4 of the distillation product of the reaction product of Example X containing the compound having the structure:

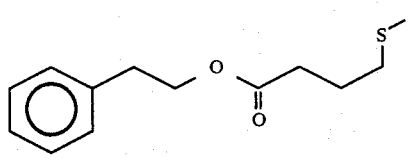

(Conditions: 8'×0.25" carbowax column programmed at 220° C. isothermal).

Figure 18:
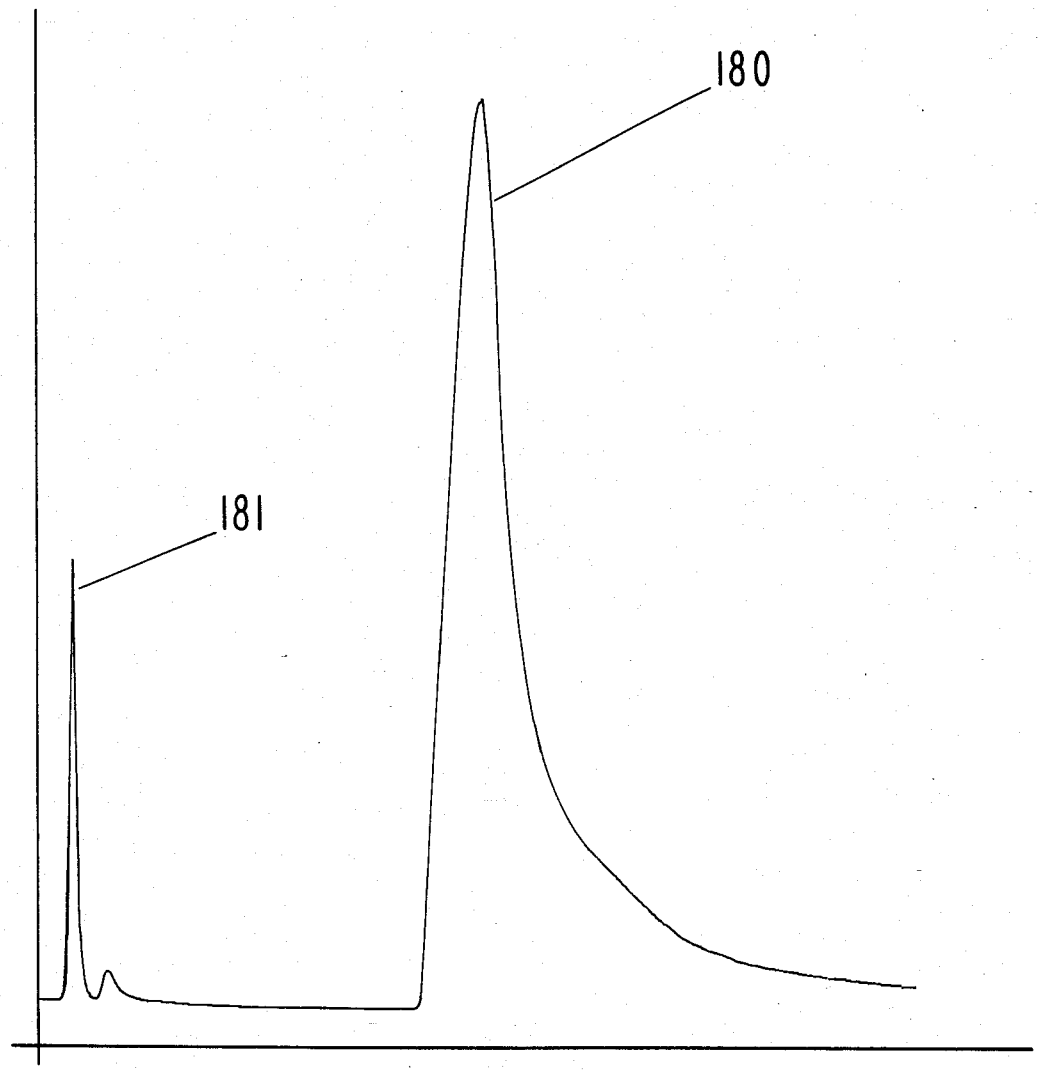

FIG. 18 is the GLC profile for fraction 5 of the distillation product of the reaction product of Example X containing the compound having the structure:

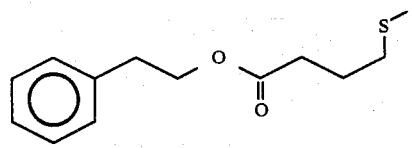

(Conditions: 8'×0.25" carbowax column programmed at 220° C. isothermal).

Figure 19:
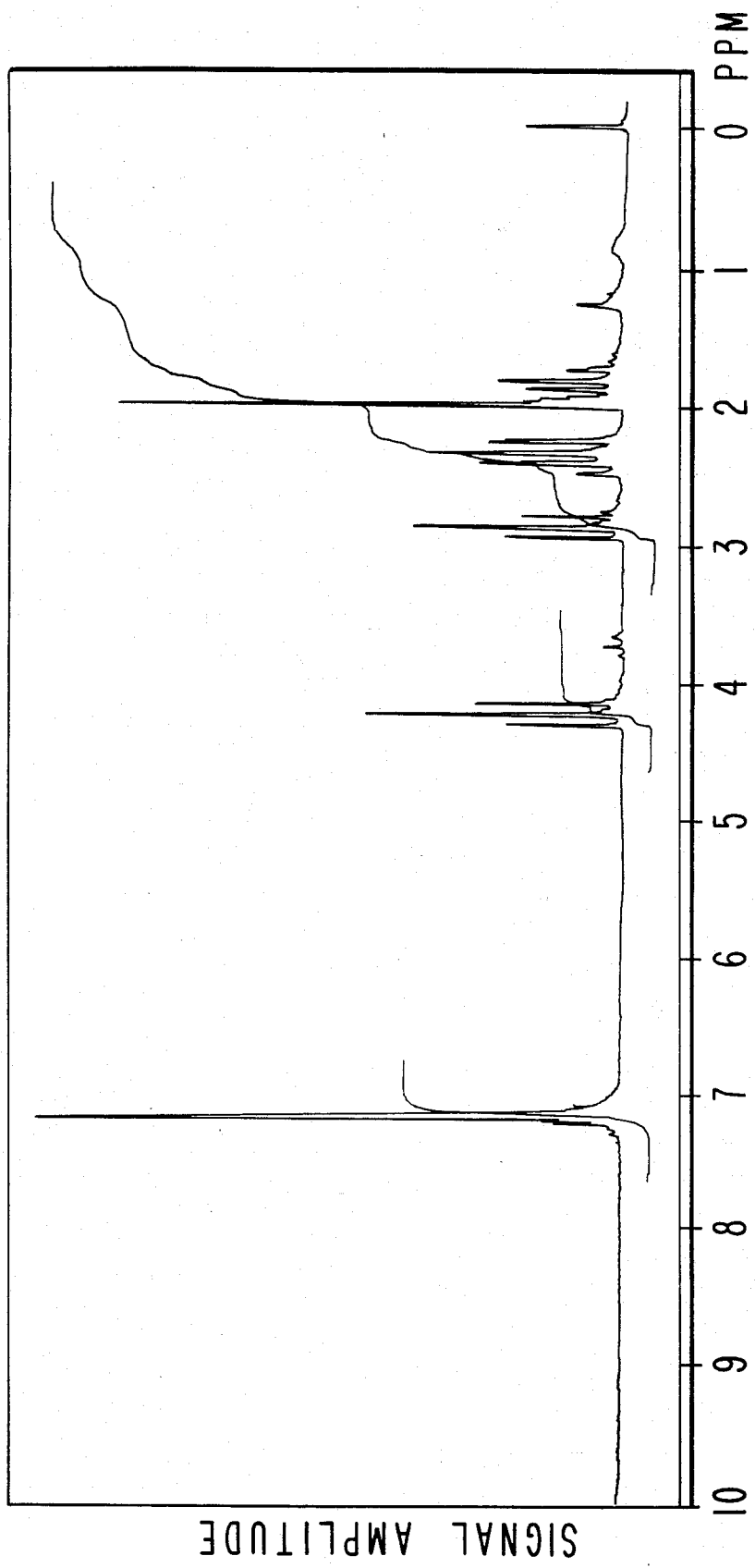

FIG. 19 is the NMR spectrum for fraction 4 of the distillation product of the reaction product of Example X containing the compound having the structure:

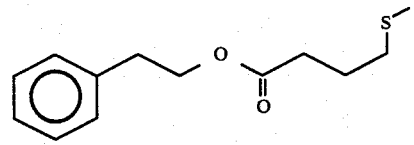

(Conditions: Field strength: 100 MHz; solvent: CFCl₃).

DETAILED DESCRIPTION OF THE DRAWINGS

FIG. 3 is the GLC profile for the crude reaction product of Example III containing the compound having the structure:

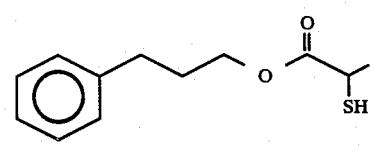

(Conditions: 8'×0.25" carbowax column programmed at 220° C. isothermal).

The peak indicated by reference numeral 30 is the peak for the compound having the structure:

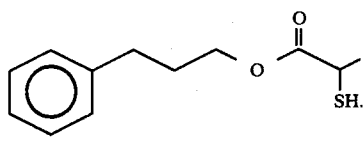

FIG. 5 is the GLC profile for the crude reaction product of Example IV containing the compound having the structure:

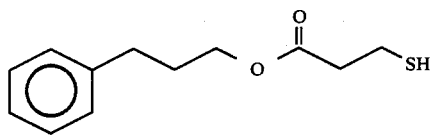

(Conditions: 8'×0.25" carbowax column programmed at 220° C. isothermal).

The peak indicated by reference numeral 50 is the peak for the compound having the structure:

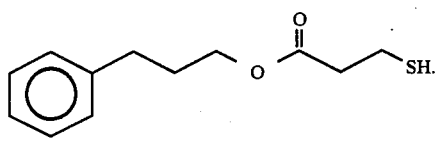

FIG. 10 is the GLC profile for the crude reaction product of Example VII containing the compound having the structure:

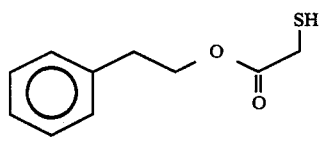

(Conditions: 8'×0.25" carbowax column programmed at 220° C. isothermal).

The peak indicated by reference numeral 100 is the peak for the compound having the structure:

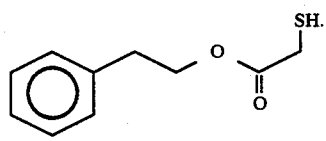

FIG. 12 is the GLC profile for the crude reaction product of Example VIII containing the compound having the structure:

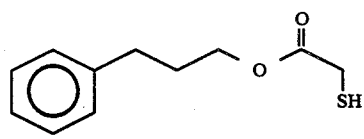

(Conditions: 8'×0.25" carbowax column programmed at 220° C. isothermal).

The peak indicated by reference numeral 120 is the peak for the compound having the structure:

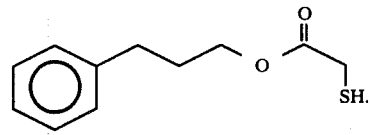

FIG. 14 is the GLC profile for fraction 3 of the distillation product of the reaction product of Example IX containing the compound having the structure:

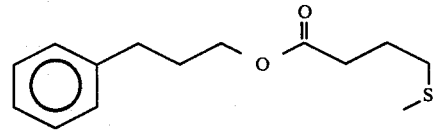

(Conditions: 8'×0.25" carbowax column programmed at 220° C. isothermal).

The peak indicated by reference numeral 140 is the peak for the compound having the structure:

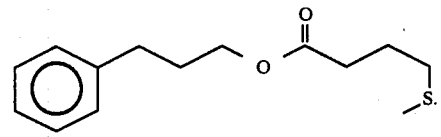

FIG. 15 is the GLC profile for fraction 4 of the distillation product of the reaction product of Example IX containing the compound having the structure:

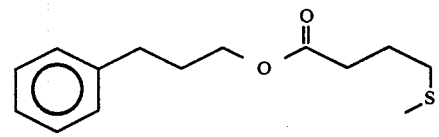

(Conditions: 8'×0.25" carbowax column programmed at 220° C. isothermal).

The peak indicated by reference numeral 150 is the peak for the acetone reaction solvent.

The peak indicated by reference numeral 151 is the peak for the reaction product having the structure:

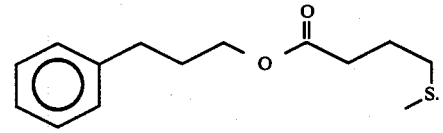

FIG. 18 is the GLC profile for fraction 5 of the distillation product of the reaction product of Example X containing the compound having the structure:

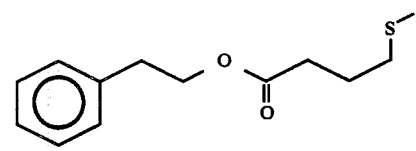

(Conditions: 8'×0.25" carbowax column programmed at 220° C. isothermal).

The peak indicated by reference numeral 180 is the peak for the product of reaction having the structure:

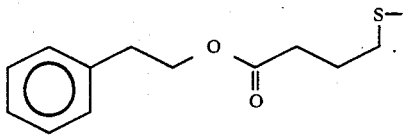

The peak indicated by reference numeral 181 is the peak for the reaction solvent, acetone.

THE INVENTION

The present invention provides thioalkanoic acid esters of phenylalkanols useful for augmenting or enhancing the aroma or taste of foodstuffs, said thioalkanoic acid esters of phenylalkanols being defined according to the structure:

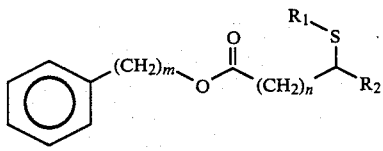

wherein M represents an integer selected from the group consisting of 1, 2 or 3; N is 0, 1 or 2; $R_1$ represents methyl or hydrogen and $R_2$ represents methyl or hydrogen as well as methods for augmenting, enhancing or modifying the organoleptic properties, e.g., taste and aroma of said foodstuffs.

The thioalkanoic acid esters of phenylalkanols of our invention augment or enhance floral, rosy, roasted, peanut, roasted peanut, sesame seed, roasted almond, sulfury, roasted sesame, oniony, durian, charbroiled, burnt, coconut/macaroon, beer, yeasty and hydrolyzed vegetable protein-like aroma and taste nuances making them useful for augmenting or enhancing flavors for such foodstuffs as roasted peanut, peanut butter, caramel, cocoa, chocolate, roasted almond, roasted nuts, sesame seed, coffee, grape, cashew juice, hazel nut, durian, burnt, yeast, beer and black bread flavored foodstuffs.

The thioalkanoic acid esters of phenylalkanols of our invention may be prepared by means of a standard esterification reaction between an alcohol having the structure:

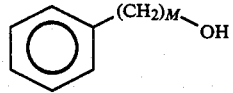

with a mercapto or alkylthio alkanoic acid having the structure:

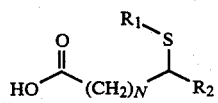

in the presence of a protonic acid such as para-toluene sulfonic acid or in the absence of such acid at temperatures in the range of from about 100° C. up to about 150° C.; preferably at reflux conditions at atmospheric pressure. Pressures higher than atmospheric pressure may be utilized thereby giving rise to higher temperatures of reaction and shorter time periods of reaction. The time of reaction may vary from about three hours up to about 15 hours depending upon the temperature of reaction.

Accordingly, the reaction taking place may be shown generically, thus:

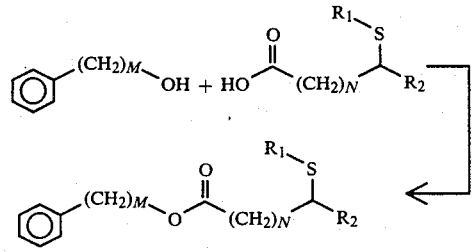

wherein M represents an integer selected from the group consisting of 1, 2 or 3; N is 0, 1 or 2; $R_1$ represents methyl or hydrogen and $R_2$ represents methyl or hydrogen.

In the alternative, a "trans-esterification" reaction may take place wherein the alcohol having the structure:

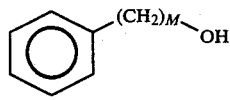

may be reacted with the ester having the structure:

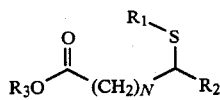

wherein $R_3$ is lower alkyl, e.g, methyl, ethyl or propyl, in the presence of a catalyst of the formula:

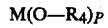

wherein M represents alkali metal such as sodium potassium or lithium or aluminum and $R_4$ represents lower alkyl, e.g., methyl, ethyl, isopropyl, n-propyl, n-butyl, t-butyl or secondary butyl and P is either 1 or 3 with the proviso that P is 1 when M is alkali metal and P is 3 when M is aluminum. The "trans-esterification" reaction takes place at a temperature in the range of from about 80° C. up to about 110° C. at atmospheric pressure. The reaction takes place in the presence of an inert solvent such as acetone and the inert solvent is provided as an initial diluent for the catalyst having the formula:

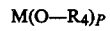

Normally, the catalyst having the formula:

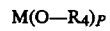

is added to the reaction mass in a 25% solution in the solvent. The solvent is an inert solvent such as methyl alcohol, ethyl alcohol, isopropyl alcohol or acetone. The time of reaction may vary from about 0.10 hours up to about 5 hours depending on the temperature of reaction.

At the end of the reaction the reaction mass is worked up by admixing with a solvent such as methylene dichloride, washing the resulting solution and drying the resulting washed solution over such materials as anhydrous sodium sulfate.

The resulting mixture is then fractionally distilled as is the case in the standard esterification reaction, supra. The "trans-esterification" reaction may be shown thusly:

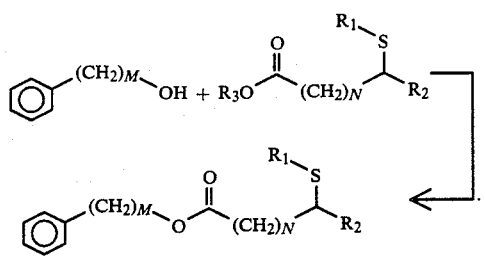

Examples of reaction products of our invention and their organoleptic properties are as follows:

TABLE I

| STRUCTURE OF REACTION PRODUCT | ORGANOLEPTIC PROPERTIES; USEFUL CONCENTRATIONS; AND END USE IN FOODSTUFF |
|---|---|
| Compound having the structure:<br>[structure]<br>prepared according to Example I | A floral, rosy and roasted peanut aroma and taste profile at 10 ppm causing it to be useful in roasted peanut, peanut butter, caramel, cocoa, chocolate and roasted almond flavored foodstuffs. |
| The compound having the structure:<br>[structure]<br>prepared according to Example II | A roasted, roasted peanut and sesame seed aroma and taste profile at 0.1 ppm causing it to be useful in roasted nut, sesame seed and coffee flavored foodstuffs. |
| The compound having the structure:<br>[structure]<br>prepared according to Example III | A roasted and roasted almond aroma and taste profile at 0.1 ppm causing it to be useful in roasted almond and roasted peanut flavored foodstuffs. |
| The compound having the structure:<br>[structure]<br>prepared according to Example IV. | A roasted, sulfury and roasted almond aroma and taste profile at 0.1 ppm. |
| The compound having the structure:<br>[structure]<br>prepared according to Example V. | A roasted, roasted sesame, sulfury and roasted almond aroma and taste profile at 0.01 ppm causing it to be useful in roasted almond, sesame and grape flavored foodstuffs. |
| The compound having the structure:<br>[structure]<br>prepared according to Example VI | A floral, roasted, oniony and durian aroma profile with a floral, roasted, hazel nut, onion, and durian taste profile at 0.01 ppm causing it to be useful in cashew juice, hazel nut and durian flavored foodstuffs. |
| The compound having structure:<br>[structure]<br>prepared according to Example VII | A charbroiled, roasted and sulfury aroma and taste profile at 0.02 ppm causing it to be useful in roasted, roasted almond, roasted peanut and roasted meat-flavored foodstuffs. |
| The compound having the structure:<br>[structure]<br>prepared according to Example VIII | A roasted, sulfury and burnt aroma and taste profile at 0.1 ppm. |
| The compound having structure:<br>[structure]<br>prepared according to Example IX | A sulfury, coconut/macaroon and durian aroma and taste profile at 5 ppm. |
| The compound having structure:<br>[structure]<br>prepared according to Example X | A beer, yeasty, floral and hydrolyzed vegetable protein-like aroma and taste profile at 5 ppm causing it to be useful in yeast, beer and black bread flavored foodstuffs. |

Thus, the thioalkanoic acid esters of phenylalkanols of our invention can be used to alter, vary, fortify, modify, enhance or otherwise improve the organoleptic properties including flavor and/or aroma of a wide variety of materials which are ingested, consumed or otherwise organoleptically sensed.

The term "alter" in its various forms will be understood herein to mean the supplying or imparting of a flavor character or note to an otherwise bland, relatively tasteless substance or augmenting an existing flavor characteristic where the natural flavor is deficient in some regard or supplementing the existing flavor or aroma impression to modify the organoleptic character. The materials which are so altered are generally referred to herein as consumable materials.

Such thioalkanoic acid esters of phenylalkanols of our invention are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs include meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetables, cereals, soft drinks, snack foods, dog and cat foods, other veterinary products, and the like.

When the thioalkanoic acid esters of phenylalkanols of this invention are used in a food flavoring composition, they can be combined with conventional flavoring materials or adjuvants. Such co-ingredients or flavoring adjuvants are well known in the art for such use and have been extensively described in the literature. Apart from the requirement that any such adjuvant material is ingestibly acceptable, and thus non-toxic or otherwise non-deleterious, conventional materials can be used and broadly include other flavor materials, vehicles, stabilizers, thickeners, surface active agents, conditioners and flavor intensifiers.

Examples of preferred co-flavoring adjuvants are:
Methyl thiazole alcohol (4-methyl-5-$\beta$-hydroxyethyl thiazole);
2-Methyl butanethiol;
4-Mercapto-2-butanone;
3-Mercapto-2-pentanone;
1-Mercapto-2-propanone;
Benzaldehyde;
Furfural;
Furfuryl alcohol;
2-Mercapto propionic acid;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
2,5-Dimethyl-3-acetyl furan
2,5-Dimethyl-3-acetyl thiophene
2,4-Decadienal;
Guiacol;
Phenyl acetaldehyde;
$\delta$-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Monopotassium glutamate;
Sulphur-containing amino acids, e.g., cysteine;
Hydrolyzed vegetable protein;
2-Methylfuran-3-thiol;
2-Methyldihydrofuran-3-thiol;
2,5-Dimethylfuran-3-thiol;
Hydrolyzed fish protein;
Allyl propenyl disulfide;
Allyl propenyl trisulfide;
Methyl propenyl disulfide;
Methyl propenyl trisulfide;
Allyl methyl disulfide;
Diallyl disulfide;
Diallyl trisulfide;
Trimethyl pyrazine;
Methyl methylthio pyrazine;
Methyl methoxy pyrazine;
Nor-methyl jasmonate (described in U.S. Pat. No. 4,294,863 issued on Oct. 13, 1981);
2-Methyl-4-n-propyl-1,3-oxathiane;
2-Methyl-6-n-propyl-1,3-oxathiane;
Guava extract;
Mango extract;
Vanillin;
Phenyl acetaldehyde;
Benzyl acetate;
Benzyl alcohol;
Ethyl-3-methyl-3-phenyl-glycidate;
Heliotropin;
Ocimene;
Linalool;
Cis-allocimene;
Trans-allocimene;
Myrcene;
Gamma-hexalactone; and
Gamma-heptalactone The thioalkanoic acid esters of phenylalkanols of our invention or the compositions incorporating them, as mentioned above, can be combined with one or more vehicles or carriers for adding them to the particular product to be flavored. Vehicles can be edible or otherwise suitable materials such as ethyl alcohol, propylene glycol, water and the like. Carriers include materials such as gum arabic, carrageenan, guar gum, xanthan gum and the like. The thioalkanoic acid esters of phenylalkanols of our invention can be incorporated with the carriers by conventional means such as spray-drying, drum-drying and the like. Such carriers can also include materials for coacervating the thioalkanoic acid esters of phenylalkanols of our invention (and other flavoring ingredients, as present) to provide encapsulated products. When the carrier is an emulsion, the flavoring composition can also contain emulsifiers such as mono- and diglycerides or fatty acids and the like. With these carriers or vehicles, the desired physical form of the composition can be prepared.

The quantity of thioalkanoic acid esters of phenylalkanols utilized should be sufficeint to impart the desired flavor characteristic to the product, but on the other hand, the use of an excessive amount of the derivative is not only wasteful and uneconomical, but in some instances too large of a quantity may unbalance the flavor or other organoleptic properties of the product consumed. The quantity used will vary depending upon the ultimate foodstuff; the amount and type of flavor initially present in the foodstuff; the further process or treatment steps to which the foodstuff will be subjected; regional and other preference factors; the type of storage, if any, to which the product will be subjected; and the preconsumption treatment, such as baking, frying and so on, given to the product by the ultimate consumer. Accordingly, the terminology "effective amount" and "sufficient amount" is understood in the context of the present invention to be quantitatively adequate to alter the flavor of the foodstuff.

It is accordingly preferred that the ultimate composition contain from about 0.001 parts per million (ppm) to about 250 ppm of thioalkanoic acid esters of phenylalkanols thereof. More particularly, in food compositions it is desirable to use from about 0.001 to 100 ppm for enhancing flavors and in certain preferred embodiments of the invention, from about 0.001 to 50 ppm of the derivatives are included to add positive flavors to the finished product.

The amount of thioalkanoic acid esters of phenylalkanols thereof of our invention to be utilized in flavoring compositions can be varied over a wide range depending upon the particular quality to be added to the foodstuff. Thus, amounts of one or more derivatives according to the present invention of from about 0.04 ppm up to 80 or 90 percent of the total flavoring composition can be incorporated in such compositions. It is generally found to be desirable to include from about 0.05 ppm up to about 0.1 percent of the thioalkanoic acid esters of phenylalkanols in such compositions.

The following examples are given to illustrate embodiments of the invention as it is preferred to practice it. It will be understood that these examples are illustrative and the invention is not to be considered as restricted thereto except as indicated in the appended claims.

All parts, proportions, percentages and ratios used herein are by weight unless otherwise indicated.

EXAMPLE I

PREPARATION OF PHENETHYL-2-MERCAPTOPROPIONATE

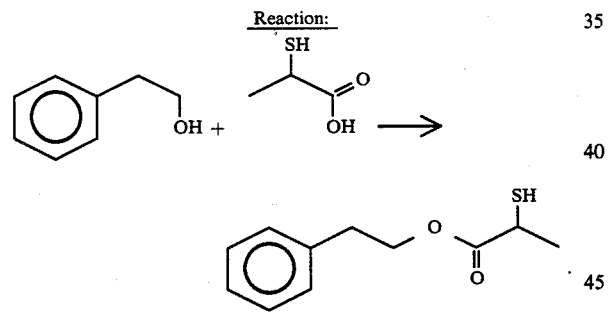

Into a 250 cc reaction flask equipped with stirrer, thermometer and reflux condenser are placed 120 grams phenylethyl alcohol; 26 grams 3-mercaptopropionic acid; and 0.5 grams of para-toluene sulphonic acid. With stirring, the reaction mass is heated to reflux and refluxed for a period of 8 hours. At the end of the 8 hour period, the reaction mass is mixed with 200 ml diethyl ether and washed with two 100 ml portions of 10% aqueous sodium bicarbonate followed by one 100 ml portion of water. The organic phase is separated and dried and the solvents are recovered on a Buchi evaporator. The resulting product is then distilled using a micro distillation apparatus yielding the following fractions:

| FRACTION NO. | VAPOR TEMP (°C.) | LIQUID TEMP. (°C.) | VACUUM PRESSURE mm/Hg | WEIGHT OF FRACTION |
|---|---|---|---|---|
| 1 | 59 | 75 | 5.0 | 12.9 |
| 2 | 81 | 88 | 5.0 | 24.9 |
| 3 | 90 | 95 | 5.0 | 28.8 |

-continued

| FRACTION NO. | VAPOR TEMP (°C.) | LIQUID TEMP. (°C.) | VACUUM PRESSURE mm/Hg | WEIGHT OF FRACTION |
|---|---|---|---|---|
| 4 | 90 | 130 | 5.0 | 17.0 |

FIG. 1 is the NMR spectrum for the compound having the structure:

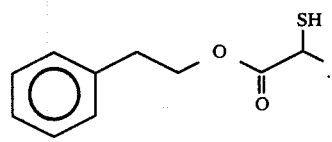

The compound having the structure:

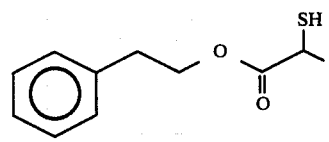

has a floral, rosy and roasted peanut aroma and taste profile at 10 ppm causing it to be useful in roasted peanut, peanut butter, caramel, cocoa, chocolate and roasted almond flavored foodstuffs.

FIG. 1 is the NMR spectrum for the compound having the structure:

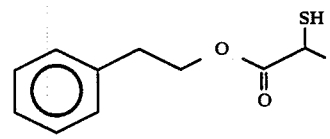

(Conditions: Field strength: 100 MHz; solvent: CFCl₃).

EXAMPLE II

PREPARATION OF PHENETHYL-3-MERCAPTOPROPIONATE

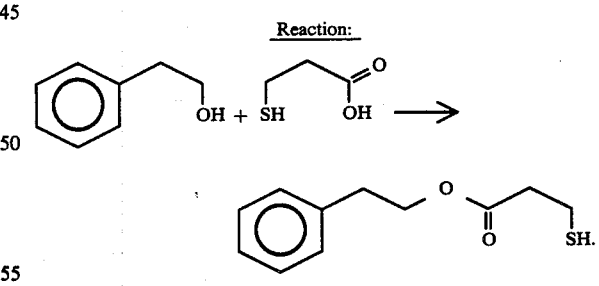

Into a 250 ml reaction flask equipped with stirrer, thermometer and reflux condenser are placed 120 grams of phenylethyl alcohol; 26 grams of 3-mercaptopropionic acid; and 0.5 grams of para-toluene sulphonic acid. The reaction mass is heated to reflux and while refluxing is stirred for a period of 9 hours. At the end of the 9 hour period, the reaction mass is cooled to room temperature and 200 ml diethyl ether is admixed with the reaction mass. The resulting mixture is then washed with two 100 ml portions of 10% sodium bicarbonate solution (aqueous) followed by one 100 ml portion of water. The aqueous phase is separated from the organic phase and the organic phase is dried over anhydrous sodium sulfate and the solvent is recovered using a Buchi evaporator. The resulting product is then distilled on a micro distillation apparatus yielding the following fractions:

| FRACTION NO. | VAPOR TEMP (°C.) | LIQUID TEMP. (°C.) | VACUUM PRESSURE mm/Hg | WEIGHT OF FRACTION |
|---|---|---|---|---|
| 1 | 75 | 87 | 5.0 | 20.6 |
| 2 | 75 | 88 | 5.0 | 21.4 |
| 3 | 77 | 88 | 5.0 | 13.7 |
| 4 | 78 | 89 | 5.0 | 23.4 |
| 5 | 95 | 120 | 5.0 | 11.4 |

The resulting product as confirmed by NMR, GLC, IR and mass spectral analyses has the structure:

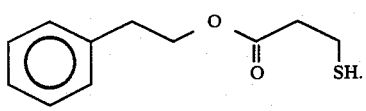

The resulting product has a roasted, roasted peanut and sesame seed aroma and taste profile at 0.1 ppm causing it to be useful in roasted nut, sesame seed and coffee flavored foodstuffs.

FIG. 2 is the NMR spectrum for the compound having the structure:

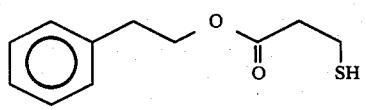

(Conditions: Field strength: 100 MHz; solvent: CFCl$_3$).

EXAMPLE III

PREPARATION OF PHENYLPROPYL-2-MERCAPTOPROPIONATE

Reaction:

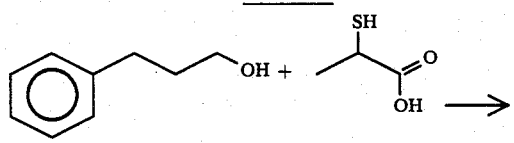

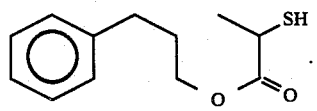

Into a 100 ml reaction flask equipped with reflux condenser, hot plate (with stirring apparatus contained within) and spin bar are placed 13.6 grams phenylpropyl alcohol; 4.0 grams of 2-mercaptopropionic acid; and 0.1 grams of para-toluene sulphonic acid. The reaction mass is maintained at reflux for a period of 9 hours with stirring. At the end of the 9 hour period, the reaction mass is cooled and fractionally distilled on a micro distillation apparatus yielding the compound having the structure:

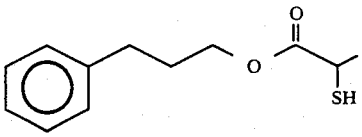

(as confirmed by GLC, mass spectral, NMR and IR analyses).

FIG. 3 is the GLC profile for the crude reaction product containing the compound having the structure:

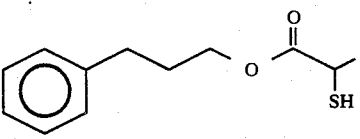

The peak indicated by reference numeral 30 is the peak for the compound having the structure:

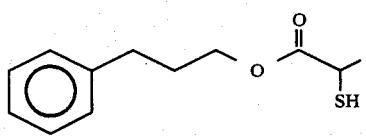

(Conditions: 8'×0.25" carbowax column programmed at 220° C. isothermal).

FIG. 4 is the GLC profile for the compound having the structure:

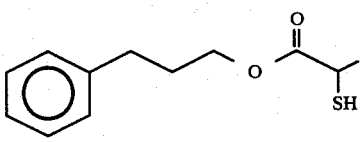

(Conditions: Field strength: 100 MHz; solvent: CFCl$_3$).

The compound having the structure:

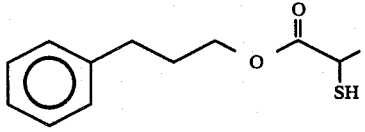

has a roasted and roasted almond aroma and taste profile at 0.1 ppm causing it to be useful in roasted almond and roasted peanut flavored foodstuffs.

EXAMPLE IV

PREPARATION OF PHENYLPROPYL-3-MERCAPTOPROPIONATE

Reaction:

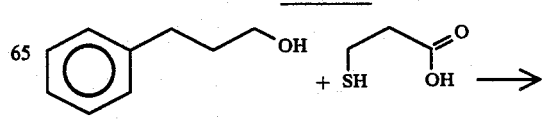

-continued

Reaction:

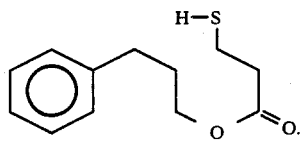

Into a 100 ml reaction flask equipped with reflux condenser, hot plate (with stirring apparatus within) and spin bar are placed 13.6 grams phenylpropyl alcohol; 4.0 grams of 3-mercaptopropionic acid; and 0.1 grams of para-toluene sulphonic acid. The reaction mass is heated to reflux and refluxed for a period of 10 hours with stirring. At the end of the 10 hour period, the reaction mass is cooled to room temperature and fractionally distilled on a micro distillation apparatus yielding the compound having the structure:

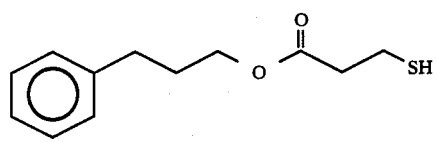

(as confirmed by GLC, NMR, mass spectral and IR analyses).

The resulting compound having the structure:

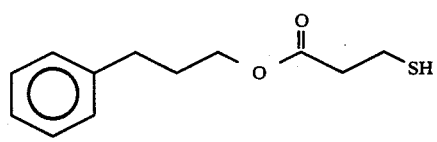

has a roasted, sulfury and roasted almond aroma and taste profile at 0.1 ppm.

FIG. 5 is the GLC profile for the crude reaction product containing the compound having the structure:

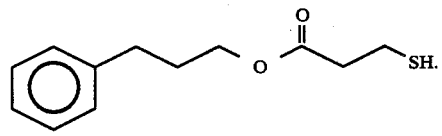

The peak indicated by reference numeral 50 is the peak for the product having the structure:

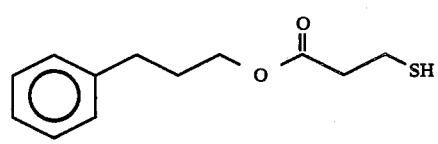

(Conditions: 8'×0.25" carbowax column programmed at 220° C. isothermal).

FIG. 6 is the NMR spectrum for the compound having the structure:

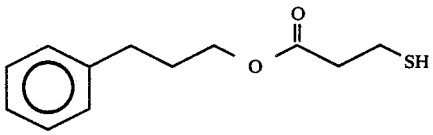

(Conditions: Field strength: 100 MHz; solvent: CFCl$_3$).

EXAMPLE V

PREPARATION OF BENZYL-3-MERCAPTOPROPIONATE

Reaction:

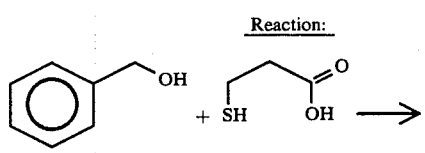

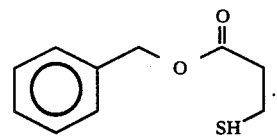

Into a 100 ml flask equipped with reflux condenser, thermometer, hot plate (with stirring apparatus included within) and spin bar are placed 21.6 grams of benzyl alcohol; 29.6 grams of 3-mercaptopropionic acid; and 0.5 grams of para-toluene sulphonic acid.

The reaction mass is heated to reflux, and with stirring, refluxed for a period of 9 hours. At the end of the 9 hour period the reaction mass is cooled to room temperature and distilled using a micro distillation apparatus yielding the following fractions:

| FRACTION NO. | VAPOR TEMP (°C.) | LIQUID TEMP. (°C.) | VACUUM PRESSURE mm/Hg |
|---|---|---|---|
| 1 | 35 | 100 | 760 (atm) |
| 2 | 123 | 130 | 5 |
| 3 | 152 | 159 | 4 |
| 4 | 170 | 179 | 4 |
| 5 | 187 | 205 | 4 |

FIG. 7 is the NMR spectrum for the compound having the structure:

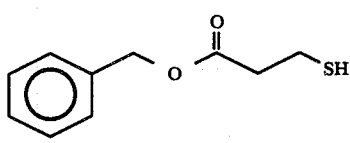

(Conditions: Field strength: 100 MHz; solvent: CFCl$_3$).

The resulting product has a roasted, roasted sesame, sulfry and roasted almond aroma and taste profile at 0.01 ppm causing it to be useful in roasted almond, sesame and grape-flavored foodstuffs.

EXAMPLE VII

PREPARATION OF BENZYL-2-MERCAPTOPROPIONATE

Reaction:

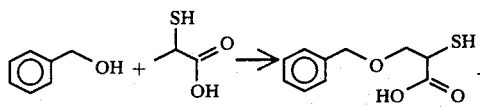

Into a 100 ml reaction flask equipped with thermometer, reflux condenser, hot plate (equipped with magnetic stirring apparatus) and spin bar are placed 21.6 grams benzyl alcohol; 29.6 grams of 2-mercaptopropionic acid; and 0.5 grams of para-toluene sulphonic acid.

The reaction mass is heated to reflux and refluxed for a period of 9 hours. At the end of the 9 hour period the reaction mass is cooled to room temperature and fractionally distilled on a micro distillation apparatus to yield the compound having the structure:

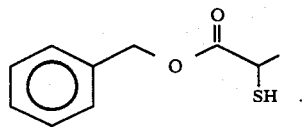

The compound having the structure:

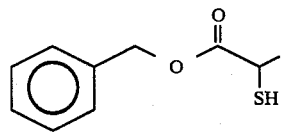

has a floral, roasted, oniony and durian aroma profile and a floral, roasted, hazel nut, onion and durian taste profile at 0.01 ppm causing it to be useful in cashew juice, hazel nut and durian flavored foodstuffs.

FIG. 8 is the GLC profile for the crude reaction product containing the compound having the structure:

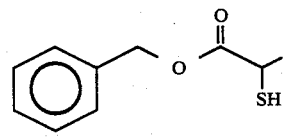

(Conditions: 8'×0.125" SE-30 column programmed at 100°–220° C. at 8° C. per minute).

FIG. 9 is the NMR spectrum for the compound having the structure:

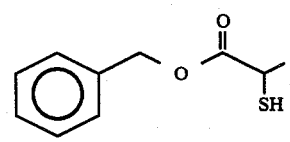

(Conditions: Field strength: 100 MHz; solvent: CFCl$_3$).

EXAMPLE VII

PREPARATION OF PHENYLETHYL-MERCAPTOACETATE

Reaction:

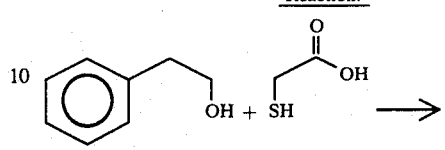

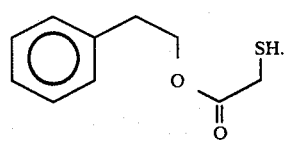

Into a 100 ml reaction flask equipped with thermometer, reflux condenser, hot plate (with magnetic stirring apparatus included within) and spin bar are placed 12.2 grams of phenylethyl alcohol; 23.0 grams mercaptoacetic acid; and 0.5 grams of para-toluene sulphonic acid.

The reaction mass with stirring is heated to reflux and maintained at reflux for a period of 9 hours. At the end of the 9 hour period, the reaction mass is cooled to room temperature and distilled on a micro distillation apparatus yielding the compound having the structure:

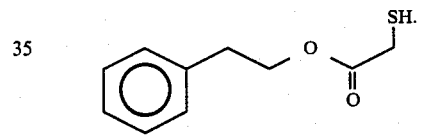

The compound having the structure:

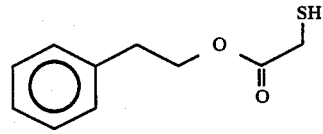

has a charbroiled, roasted and sulfury aroma and taste profile at 0.02 ppm causing it to be useful in roasted, roasted almond, roasted peanut and roasted meat-flavored foodstuffs.

FIG. 10 is the GLC profile for the crude reaction product containing the compound having the structure:

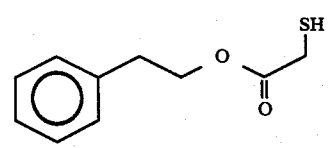

(Conditions: 8'×0.25" carbowax column programmed at 220° C. isothermal).

The peak indicated by reference numeral 100 is the peak for the compound having the structure:

FIG. 11 is the NMR spectrum for the compound having the structure:

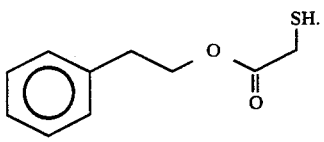

(Conditions: Field strength: 100 MHz; solvent: CFCl₃).

EXAMPLE VIII

PREPARATION OF PHENYLPROPYL MERCAPTOACETATE

Reaction:

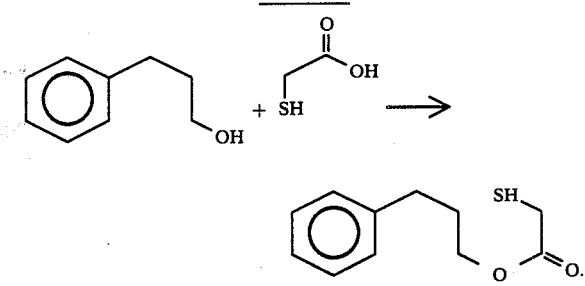

Into a 100 ml flask equipped with reflux condenser, thermometer, hot plate (including magnetic stirring apparatus within) and spin bar are placed 13.6 grams phenylpropyl alcohol; 4 grams of mercaptoacetic acid; and 0.1 grams para-toluene sulphonic acid.

The reaction mass is heated to reflux with stirring and maintained at reflux for a period of 10 hours. At the end of the 10 hour period the reaction mass is cooled to room temperature and the product containing the compound having the structure:

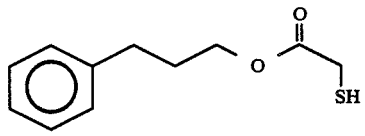

is distilled on a micro distillation apparatus yielding the compound having the structure:

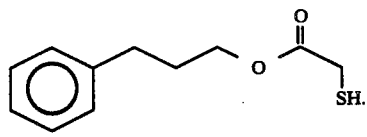

The compound having the structure:

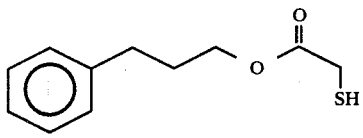

has a roasted, sulfury and burnt aroma and taste profile at 0.1 ppm.

FIG. 12 is the GLC profile for the crude reaction product containing the compound having the structure:

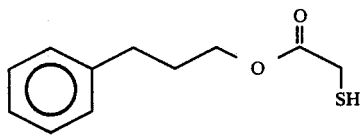

(Conditions: 8'×0.25" carbowax column programmed at 220° C. isothermal).

The peak indicated by reference numeral 120 is the peak for the compound having the structure:

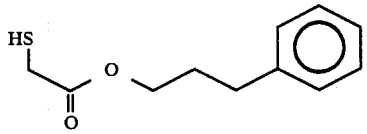

FIG. 13 is the NMR spectrum for the compound having the structure:

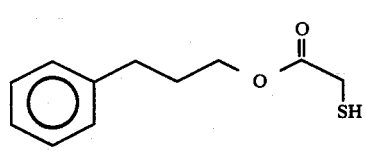

(Conditions: Field strength: 100 MHz; solvent: CFCl₃).

EXAMPLE IX

PREPARATION OF PHENYLPROPYL(4-METHYLTHIO)BUTYRATE

Reaction:

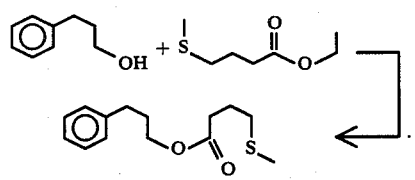

Into a 100 ml reaction flask equipped with reflux condenser, thermometer and hot plate (containing a magnetic stirring apparatus within) and spin bar are placed 10.6 grams of phenylpropyl alcohol; 8.1 grams of the ethyl ester of 4-methylthiobutyric acid; and a solution of 25% sodium methoxide in acetone (total: 0.5 grams).

The reaction mass is heated to 100° C. and maintained at 100° C. for a period of 15 minutes. At the end of the 15 minute period, the reaction mass is shown to be complete by means of GLC. The resulting product is cooled to room temperature and admixed with 50 ml methylene dichloride. The resulting mixture is then washed with two 50 ml portions of water and dried over anhydrous sodium sulfate. The resulting product is distilled on a micro distillation apparatus yielding the following fractions:

| FRACTION NO. | VAPOR TEMP (°C.) | LIQUID TEMP. (°C.) | VACUUM PRESSURE mm/Hg | WEIGHT OF FRACTION |
|---|---|---|---|---|
| 1 | 80/100 | 190/135 | 15.0 | 6.4 |
| 2 | 95 | 208 | 15.0 | 1.3 |
| 3 | 185 | 215 | 15.0 | 4.8 |
| 4 | 185 | 220 | 15.0 | 2.9 |

The resulting product has the structure:

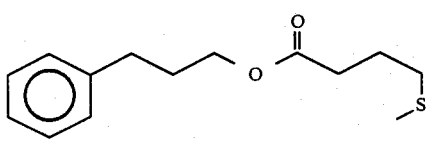

as confirmed by GLC, NMR, mass spectral and IR analyses.

The compound having the structure:

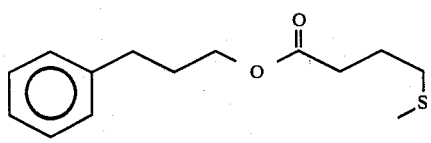

has a sulfury, coconut/macaroon and durian aroma and taste profile at 5 ppm.

FIG. 14 is the GLC profile for fraction 3 of the foregoing distillation. (Conditions: 8'×0.25" carbowax column programmed at 220° C. isothermal).

The peak indicated by reference numeral 140 is the peak for the compound having the structure:

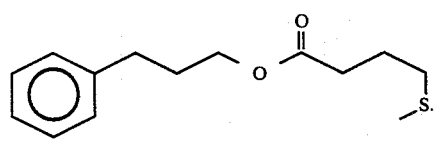

FIG. 15 is the GLC profile for fraction 4 of the foregoing distillation. (Conditions: 8'×0.25" carbowax column programmed at 220° C. isothermal).

The peak indicated by reference numeral 151 is the peak for the product having the structure:

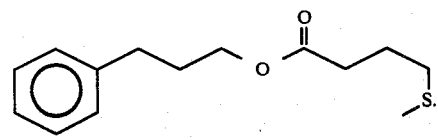

The peak indicated by reference numeral 150 is the peak for the reaction solvent (acetone).

FIG. 16 is the NMR spectrum for fraction 4 of the foregoing distillation containing the compound having the structure:

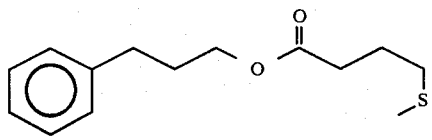

(Conditions: Field strength: 100 MHz; solvent: CFCl$_3$).

EXAMPLE X

PREPARATION OF PHENETHYL(4-METHYLTHIO)BUTYRATE

Reaction:

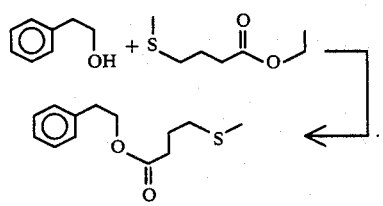

Into a 250 ml reaction flask equipped with stirrer, thermometer and reflux condenser are placed 12.6 grams of phenylethyl alcohol; 8.1 grams of the ethyl ester of 4-methylthiobutyric acid; and 0.5 grams of a 25% solution of sodium methoxide in acetone. The reaction mass with stirring is heated to 100° C. and maintained at 100° C. for a period of 15 minutes. At the end of the 15 minute period the reaction mass is cooled to room temperature and admixed with 50 ml methylene dichloride. The resulting mixture is washed with two 50 ml portions of water and dried over anhydrous sodium sulphate. The resulting product is distilled on a micro distillation apparatus yielding the following fractions:

| FRACTION NO. | VAPOR TEMP (°C.) | LIQUID TEMP. (°C.) | VACUUM PRESSURE mm/Hg | WEIGHT OF FRACTION |
|---|---|---|---|---|
| 1 | 93/85 | 113/104 | 10.0 | 3.5 |
| 2 | 90 | 140 | 10.0 | 4.4 |
| 3 | 95 | 191 | 10.0 | 1.4 |
| 4 | 163 | 196 | 10.0 | 3.8 |
| 5 | 165 | 250 | 10.0 | 1.8 |

The resulting product has the structure:

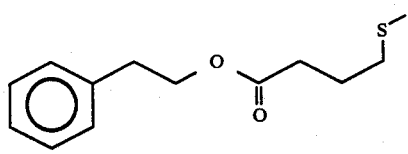

as determined by GLC, NMR, IR and mass spectral analyses.

The compound having the structure:

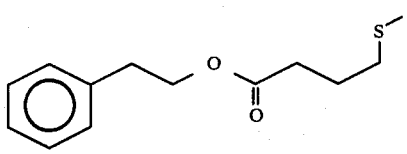

has a beer, yeasty, floral and hydrolyzed vegetable protein-like aroma and taste profile at 5 ppm causing it to be useful in yeast, beer and black bread flavored foodstuffs.

FIG. 17 is the GLC profile for fraction 4 of the foregoing distillation. (Conditions: 8'×0.25" carbowax column programmed at 220° C. isothermal).

FIG. 18 is the GLC profile for fraction 5 of the foregoing distillation. (Conditions: 8'×0.25" carbowax column programmed at 220° C. isothermal).

The peak indicated by reference numeral 180 is the peak for the product having the structure:

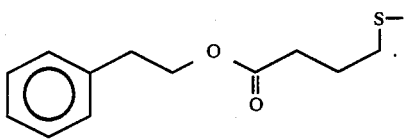

The peak indicated by reference numeral 181 is the peak for the reaction solvent, acetone.

FIG. 19 is the NMR spectrum for fraction 4 of the foregoing distillation containing the compound having the structure:

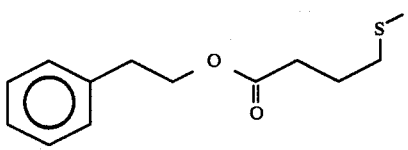

(Conditions: Field strength: 100 MHz; solvent: CFCl$_3$).

EXAMPLE XI

CHOCOLATE FLAVORED FORMULATION

The following flavor formulation is prepared:

| INGREDIENTS | PARTS BY WEIGHT |
|---|---|
| Tetramethyl pyrazine | 3.0 |
| 2-Methyl pyrazine | 4.3 |
| 3-Methyl pyrazine | 4.2 |
| 2,4-Diemthyl pyrazine | 6.2 |
| 2-Phenyl-2-butenal | 6.0 |
| 3-Phenyl-4-pentenal | 2.4 |
| The compound having the structure: 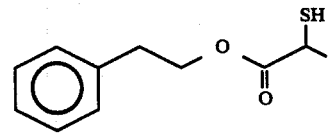 prepared according to Example I | 2.4 |

The compound having the structure:

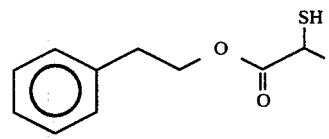

imparts a roasted, rosy, floral and peanut nuance to this cocoa flavor. When the resulting cocoa flavor is added to a cocoa drink at the level of 10 ppm a pleasant, nutty, roasted, natural cocoa nuance is imparted to this otherwise bland cocoa drink.

When the resulting flavor is added at the level of 12 ppm to a chocolate "thick-shake" a pleasant natural chocolate taste nuance is imparted to the resulting thick-shake particularly when the thick-shake is prepared using natural malt.

EXAMPLE XII

PEANUT BUTTER PREPARATION

SKIPPY ® Peanut Butter is intimately admixed at the rates of 0.1 ppm and 3 ppm with the following compounds:

Substance "A"
The compound having the structure:

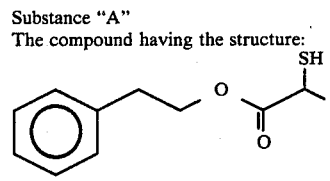

prepared according to Example I;

Substance "B"
The compound having the structure:

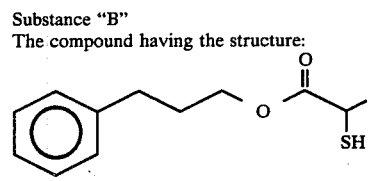

prepared according to Example III; and

Substance "C"
The compound having the structure:

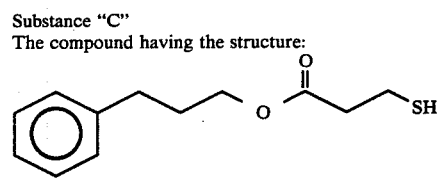

prepared according to Example IV.

In all cases the peanut butter admixed with Substances "A", "B" and "C" has a more natural roasted peanut taste nuances with interesting roasted nut nuances causing a bench panel of five members ("blind", not associated with the instant invention) to unanimously prefer the peanut butter samples containing the thioalkanoic acid esters of phenylalkanols of our invention as set forth above (substances "A", "B" and "C").

Thus, the compound having the structure:

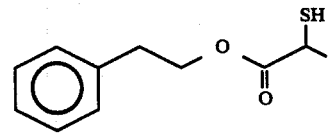

imparts to the peanut butter a floral, rosy and roasted peanut aroma and taste profile.

The compound having the structure:

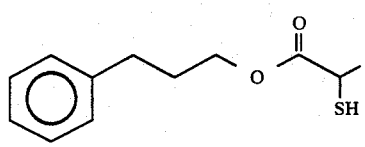

imparts a roasted and roasted almond aroma and taste profile to the resulting peanut butter.

The compound having the structure:

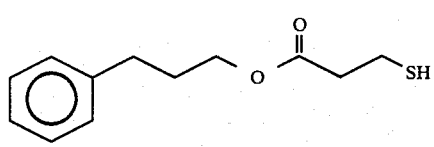

imparts to the peanut butter a roasted almond aroma and taste nuance.

EXAMPLE XIII

"HALVAH" SESAME CONFECTION

As the rate of 0.2 ppm the compound having the structure:

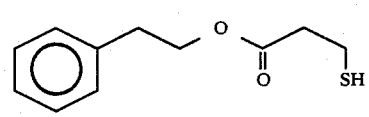

is added to "778 House of Isaac" Halvah Sauce prepared by House of Isaac Inc. of Israel (ingredients: ground sesame;
sesame oil;
sugar; and
vegetable oil).

The resulting Halvah Sauce has an excellent roasted, roasted peanut and natural sesame seed aroma and taste profile causing a blind bench panel of five members to unanimously prefer the Halvah Sause containing the compound having the structure:

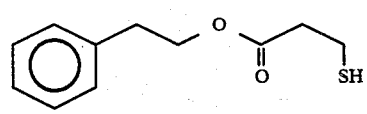

over a Halvah Sauce not containing such compound.

When the compound having the structure:

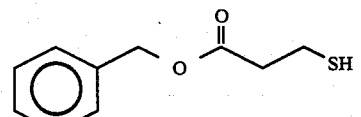

is added to the Halvah Sauce an interesting roasted sesame and roasted almond nuance is imparted to the Halvah Sauce at the level of 0.02 ppm causing a bench panel of five members ("blind", not associated with the instant invention) to unanimously prefer the Halvah Sauce containing the compound having the structure:

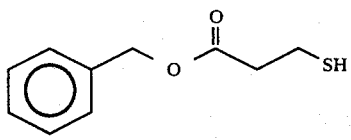

over the same Halvah Sauce without the compound having the structure:

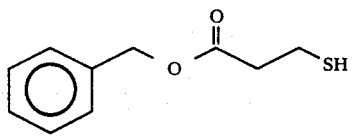

A similar effect is achieved when a 50:50 (weight:-weight) mixture of the compound having the structure:

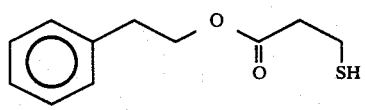

and the compound having the structure:

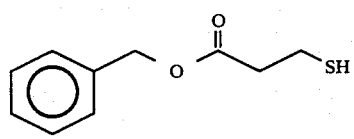

is added to the Halvah Sauce.

EXAMPLE XIV

To GOYA ® Guava Jelly (manufactured by Goya Foods Inc., of Secaucus, N.J. 07094) containing:
Guava fruit;
Guava juice;
Sugar;
Corn syrup;
Pectin; and
Citrus acid
are placed at levels of 0.5 ppm and 5 ppm the following substances:

Substance "A"
The compound having the structure:

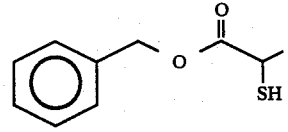

prepared according to Example VI;

Substance "B"
The compound having the structure:

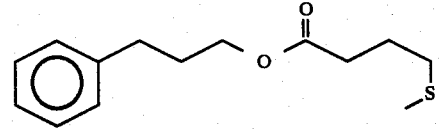

prepared according to Example IX.

The resulting Guava Jellies each have excellent "ripe natural" nuances which render the Jellies more aesthetically pleasing to a blind bench panel of five members. The blind bench panel of five members unanimously preferred the Guava Jellies containing the compounds having the structures:

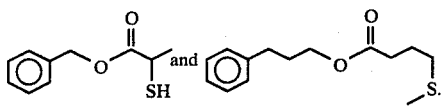

The compound having the structure:

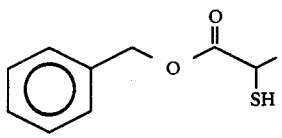

imparts a durian nuance to the Guava Jelly.

The compound having the structure:

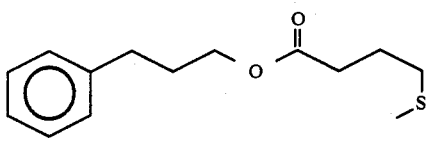

imparts a coconut and durian aroma and taste nuance to the Guava Jelly.

EXAMPLE XV

Three meat loaf type products are prepared according to the following formulation:

| INGREDIENTS | AMOUNT |
|---|---|
| TVP, minced* | 1 cup |
| Ground beef | 1 cup |
| Water | 1 cup |
| Beef suet | ¼ cup |
| Bread crumbs, dry, unflavored | 1 cup |
| Whole milk | 1 cup |
| Egg albumen | 3 tbsp. |
| Salt | 1¼ tbsp. |
| Black pepper | ¼ tbsp. |
| Catsup | ¼ cup |
| Water | 32 ml. |

*"TVP" is a texturized vegetable protein mixture made by Archer-Daniels-Midland Company.

Three separate portions prepared according to the foregoing formulations are made into three meat loaves. Loaf A contains no additional additives. Load B contains 32 ml. of fresh pressed onion juice to replace the 32 ml. of water and Loaf C contains 32 ml. fresh pressed onion juice containing 5 ppm of the compound having the structure:

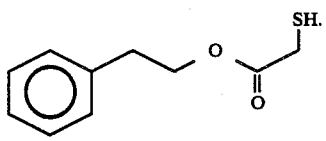

The three loaves are baked at 350° F. for one hour.

The Loaves B and C are judged superior to Loaf A because the onion character of B and C enhances the overall taste and covers the dry cardboard-like cereal character of Loaf A. However, a bench panel of five members unanimously prefers Loaf C to Loaf B because in addition to the onion character a charbroiled roasted character is imparted to the resulting meat loaf making it more aesthetically pleasing.

A similar effect is achieved when the compound having the structure:

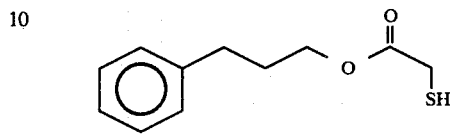

is used to replace the compound having the structure:

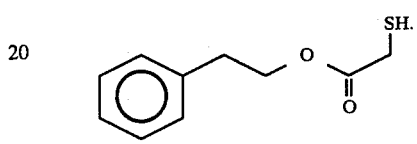

EXAMPLE XVI

The following mixture is prepared:

| INGREDIENTS | PARTS BY WEIGHT |
|---|---|
| Propyl thiopropionate prepared according to Reissue Patent No. 30,370 issued on August 12, 1980 | 30 |
| Natural onion oil | 50 |
| Compound having the structure: | 20 |

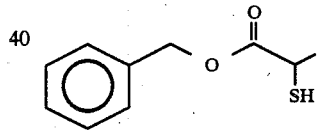

The mixture is compared with pure onion oil at the rate of 0.05 ppm in water. The mixture has fuller and fresher aroma and taste characteristics than the natural onion oil alone. The flavor strength of the mixture as compared to pure natural onion oil is the same. The mixture has a fuller and fresher aroma and taste characteristics than the combination of natural onion oil and propyl thiopropionate.

The foregoing gives rise to the conclusion that the compound having the structure:

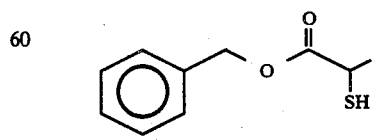

is useful in reconstituting imitation onion oils with onion aroma and taste characteristics.

The compound having the structure:

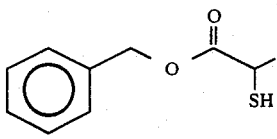

imparts a roasted, oniony and nutty aroma and taste nuance to the resulting onion oil.

EXAMPLE XVII

The compound having the structure:

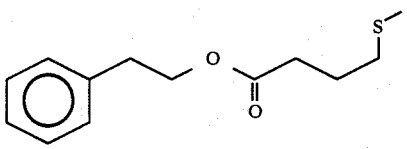

prepared according to Example X is added at the level of 5 ppm (in a propylene glycol solution containing 0.1% of the compound) at the rate of 0.9 cc to 7.3 grams of a soup base containing:

| INGREDIENTS | QUANTITY (PARTS/100 TOTAL) |
|---|---|
| Fine ground sodium chloride | 35.62 |
| Hydrolyzed vegetable protein (4 BE: Nestle's) | 27.40 |
| Monosodium glutamate | 17.81 |
| Sucrose | 10.96 |
| Beef fat | 5.48 |
| Sethness caramel color (powder B & C) | 2.73 |

The resulting mixture is added to 12 ounces of boiling water to create a soup having an excellent yeasty hydrolyzed vegetable protein-like aroma and taste with intense beer and yeasty-like nuances and an overall black bread-like character.

What is claimed is:

1. A process for augmenting or enhancing the aroma or taste of a foodstuff comprising the step of adding to said foodstuff from about 0.001 ppm up to about 250 ppm of a thioalkanoic acid ester of a phenylalkanol having the structure:

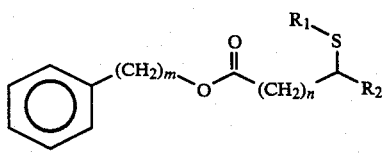

wherein M represents an integer selected from the group consisting of 1, 2 or 3; N is 0, 1 or 2; $R_1$ represents methyl or hydrogen and $R_2$ represents methyl or hydrogen.

2. The process of claim 1 wherein the thioalkanoic acid ester of the phenylalkanol has the structure:

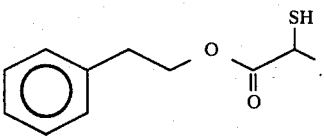

3. The process of claim 1 wherein the thioalkanoic acid ester of the phenylalkanol has the structure:

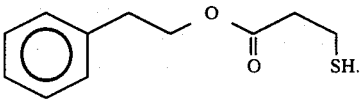

4. The process of claim 1 wherein the thioalkanoic acid ester of the phenylalkanol has the structure:

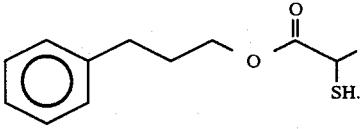

5. The process of claim 1 wherein the thioalkanoic acid ester of the phenylalkanol has the structure:

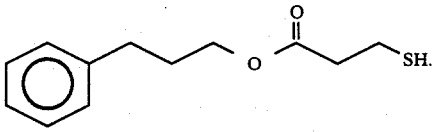

6. The process of claim 1 wherein the thioalkanoic acid ester of the phenylalkanol has the structure:

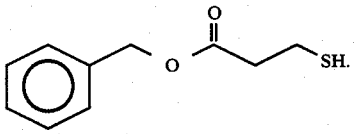

7. The process of claim 1 wherein the thioalkanoic acid ester of the phenylalkanol has the structure:

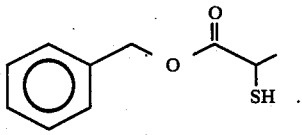

8. The process of claim 1 wherein the thioalkanoic acid ester of the phenylalkanol has the structure:

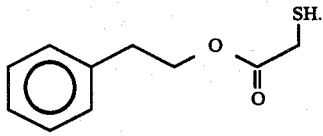

9. The process of claim 1 wherein the thioalkanoic acid ester of the phenylalkanol has the structure:

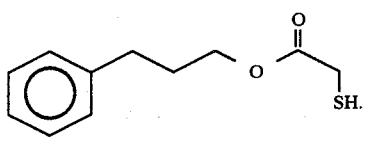
10. The process of claim 1 wherein the thioalkanoic acid ester of the phenylalkanol has the structure:
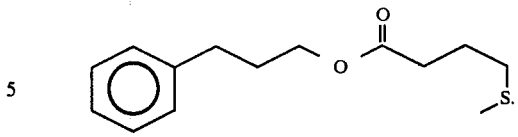
11. The process of claim 1 wherein the thioalkanoic acid ester of the phenylalkanol has the structure:
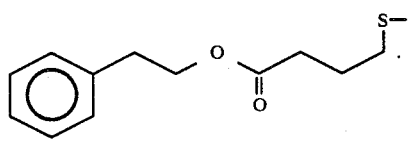
* * * * *